United States Patent [19]

Maher et al.

[11] Patent Number: 5,288,918
[45] Date of Patent: Feb. 22, 1994

[54] HYDROFORMYLATION PROCESS

[75] Inventors: John M. Maher, Charleston; James E. Babin, Hurricane; Ernst Billig, Huntington; David R. Bryant, South Charleston; Tak W. Leung, Charleston, all of W. Va.

[73] Assignee: Union Carbide Chemicals & Plastics Technology Corporation, Danbury, Conn.

[21] Appl. No.: 953,016

[22] Filed: Sep. 29, 1992

[51] Int. Cl.$^5$ .............................................. C07C 45/50
[52] U.S. Cl. .................................. 568/454; 568/451; 558/71
[58] Field of Search .................. 568/454, 451; 558/71

[56] References Cited

U.S. PATENT DOCUMENTS

| | | | |
|---|---|---|---|
| 3,533,298 | 1/1971 | Hodan et al. | 260/967 |
| 4,523,036 | 6/1985 | Cornils et al. | 568/454 |
| 4,567,306 | 1/1986 | Dennis et al. | 568/455 |
| 4,578,523 | 3/1986 | Bahrmann et al. | 568/454 |
| 4,593,126 | 6/1986 | Cornils et al. | 568/454 |
| 4,616,098 | 10/1986 | Cornils et al. | 568/454 |
| 4,650,894 | 3/1987 | Fisch et al. | 558/71 |
| 5,095,061 | 3/1992 | Chavez et al. | 524/376 |
| 5,210,318 | 5/1993 | Briggs et al. | 568/496 |

FOREIGN PATENT DOCUMENTS

| | | |
|---|---|---|
| 0466150 | 1/1992 | European Pat. Off. |
| 0518241 | 12/1992 | European Pat. Off. |
| 0348284 | 9/1960 | Switzerland |

*Primary Examiner*—Werren B. Lone
*Attorney, Agent, or Firm*—Reynold J. Finnegan

[57] ABSTRACT

An improved rhodium-organophosphite complex catalyzed hydroformylation process, the improvement comprising carrying out said process in the presence of a catalytic activity enhancing additive said additive being selected from the class consisting of added water, a weakly acidic compound, or both added water and a weakly acidic compound.

20 Claims, No Drawings

HYDROFORMYLATION PROCESS

BACKGROUND OF THE INVENTION

1. Field of the Invention

This invention relates to an improved rhodium-organophosphite complex catalyzed hydroformylation process.

2. Background Art

It is well known in the art organophosphites may be employed as catalyst ligands for rhodium based hydroformylation catalysts and that such catalysts exhibit exceptional activity and regioselectivity for producing aldehydes via olefin hydroformylation. For instance, U.S. Pat. Nos. 4,668,651 and 4,769,498 fully detail such hydroformylation.

However, despite the benefits attendant with such rhodium-organophosphite complex catalyzed hydroformylation processes, stability of the ligand and catalyst remains a primary concern. For example, U.S. Pat. No. 4,774,361 is directed to the use of an organic polymer additive to minimize or prevent the rhodium of a rhodium-diorganophosphite complex catalyst from precipitating from solution during the hydroformylation process.

Moreover, over the course of time, continuous rhodium complex catalyzed hydroformylation processes involving organophosphite ligands produce an undesirable hydroxy alkyl phosphonic acid by-product due to reaction of the organophosphite ligand and aldehyde product thereby causing a loss of ligand concentration. Moreover, the formation of such undesirable acid has been observed to be autocatalytic. The build-up of such acid over time could lead to the precipitation of an insoluble gellatinous by-product, which may plug and/or foul the recycle lines of a continuous reaction system, thus necessitating possible periodic processing shut downs or stoppages to remove such acid and/or precipitate from the system by an appropriate method, e.g., by extraction of the acid with a weak base, e.g., sodium bicarbonate. Alternatively, such a problem may be controlled by passing the liquid reaction effluent stream of the continuous liquid recycle process, either prior to or more preferably, after separation of the aldehyde product therefrom, through a weakly basic anion exchange resin bed, as disclosed, e.g., in U.S. Pat. Nos. 4,668,651; 4,717,775 and 4,769,498. A newer and more preferred method for minimizing and/or controlling the problem of such undesirable hydroxy alkyl phosphonic acid by-product resides in the employment of certain epoxide reagents to scavenge such acids, as described, e.g., in assignee's copending U.S. patent application Ser. No. 953,015 entitled "Process For Stabilizing Phosphite Ligands", filed concurrently with this present application.

An additional new problem has been observed when certain organobisphosphite ligand promoted rhodium catalysts are employed in such hydroformylation processes. This problem involves a loss in catalytic activity over time during the course of continuous use of such rhodium-bisphosphite complex catalysts, which loss can occur even in the absence of extrinsic poisons, such as chloride or sulfur compounds.

This intrinsic loss in catalytic activity observed when such organobisphosphite ligand promoted rhodium catalyst systems are employed is believed primarily or at least partly due to the formation of a class of diorganophosphite by-products which can best be described as decomposition products of the employed organobisphosphite ligands so employed. This class of diorganophosphite by-products consists of alkyl [1,1'-biaryl-2,2'-diyl] phosphites, the alkyl radical corresponding to the particular n-aldehyde produced by the hydroformylation process and the [1,1'-biaryl-2,2'-diyl] portion of the phosphite being derived from the organobisphosphite ligand employed. For example, the organobisphosphite ligand shown employed in the continuous hydroformylation process of propylene in Example 14 of U.S. Pat. No. 4,769,498 (referred to as a polyphosphite ligand in said Example 14) will in time, over the course of the continuous hydroformylation process experience an intrinsic decrease in catalytic activity because of the formation of n-butyl [1,1'-biphenyl-2,2'-diyl] phosphite. Such types of alkyl [1,1'-biaryl-2,2'-diyl] phosphites can coordinate with the rhodium metal and form complexes that are less reactive than the preferred organobisphosphite ligand promoted rhodium catalysts. In effect, such types of alkyl [1,1'-biaryl-2,2'-diyl] phosphites so derived act as a catalyst poison or inhibitor, thereby lowering the catalyst activity of the preferred organobisphosphite ligand promoted rhodium catalyst system. More simply, the loss in catalyst activity is a result of the rhodium metal not being utilized to its full potential.

DISCLOSURE OF THE INVENTION

It has now been discovered that such intrinsic catalyst deactivation of certain rhodium-bisphosphite complex catalyzed continuous hydroformylation processes may be reversed or minimized by carrying out the hydroformylation process in the presence of certain added weakly acidic compounds and/or added water.

Thus, it is an object of this invention to provide an improved continuous rhodium-bisphosphite complex catalyzed hydroformylation process wherein partially intrinsically deactivated catalyst is reactivated and/or wherein such intrinsic deactivation of the catalyst is at least minimized by carrying out the process in the presence of certain catalytic activity enhancing additives selected from the class consisting of weakly acidic compounds, added water or mixtures thereof. Other objects and advantages of this invention will become readily apparent from the following written description and appended claims.

Accordingly, a generic aspect of this invention can be described as an improved continuous hydroformylation process for producing aldehydes which comprises reacting an olefinically unsaturated compound with carbon monoxide and hydrogen in the presence of a solubilized rhodium-bisphosphite complex catalyst wherein the bisphosphite ligand of said complex catalyst is a ligand selected from the class consisting of

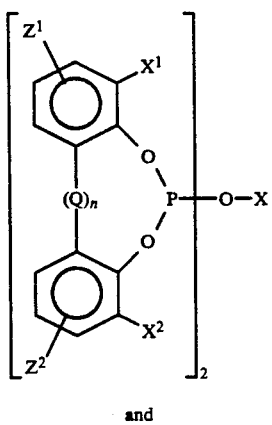

and

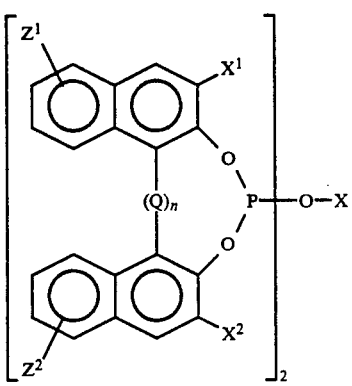

wherein each $X^1$ and $X^2$ radical individually represents a radical selected from the group consisting of hydrogen, methyl, ethyl and n-propyl; wherein each $Z^1$ and $Z^2$ radical individually represents hydrogen or an organic substituent radical containing from 1 to 18 carbon atoms; wherein each X represents a divalent radical selected from the group consisting of alkylene, alkylene-oxy-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a —$CR^5R^6$—divalent bridging group and each $R^5$ and $R^6$ radical individually represents hydrogen or a methyl radical; and wherein each n individually has a value of 0 or 1; the improvement comprising carrying out said process in the presence of minor amount of a catalytic activity enhancing additive present in the hydroformylation reaction medium of the process, said additive being selected from the class consisting of added water, a weakly acidic compound, or both added water and a weakly acidic compound.

DETAILED DESCRIPTION

Accordingly, the subject invention encompasses reversing or minimizing the intrinsic catalyst deactivation of solubilized rhodium-bisphosphite complex catalyzed, continuous hydroformylation processes for producing aldehydes, by carrying out the hydroformylation in the presence of added water and/or certain weakly acidic additives as disclosed herein.

Illustrative rhodium-bisphosphite complex catalyzed continuous hydroformylation processes in which such intrinsic catalyst deactivation may occur include hydroformylation processes such as described, e.g., in U.S. Pat. Nos. 4,668,651; 4,774,361 and 4,769,498, and U.S. patent application Ser. No. 911,518 filed Jul. 16, 1992 which is a continuation-in-part of U.S. patent applications, Ser. Nos. 748,111 and 748,112, both filed Aug. 21, 1991, wherein the bisphosphite ligand is a ligand selected from the class consisting of Formulas (I) and (II) above, the entire disclosures of said patents and applications being incorporated herein by reference thereto. Thus such hydroformylation processes and the conditions thereof are well known and it is to be understood that the particular manner in which the hydroformylation reaction is carried out and particular hydroformylation reaction conditions employed may be varied widely and tailored to meet individual needs and produce the particular aldehyde product desired.

In general, such hydroformylation reactions involve the production of aldehydes by reacting an olefinic compound with carbon monoxide and hydrogen in the presence of a solubilized rhodium-bisphosphite complex catalyst in a liquid medium that also contains a solvent for the catalyst. The process may be carried out in a continuous single pass mode or more preferably in a continuous liquid catalyst recycle manner. The recycle procedure generally involves withdrawing a portion of the liquid reaction medium containing the catalyst and aldehyde product from the hydroformylation reaction zone, either continuously or intermittently, and distilling the aldehyde product therefrom in one or more stages under normal, reduced or elevated pressure, as appropriate, in a separate distillation zone in order to recover the aldehyde product and other volatile materials in vaporous form, the non-volatilized rhodium catalyst containing residue being recycled to the reaction zone. Condensation of the volatilized materials, and separation and recovery thereof, e.g., by distillation, can be carried out in any conventional manner, the aldehyde product being passed on for further purification if desired and any recovered reactants, e.g., olefinic starting material and syn gas recycled in any desired manner to the hydroformylation zone. Likewise, the recovered non-volatilized rhodium catalyst containing residue can be recycled with or without further treatment to the hydroformylation zone in any conventional manner desired. Accordingly, the processing techniques of this invention may correspond to any known processing techniques such as heretofore employed in conventional liquid catalyst recycle hydroformylation reactions, for instance.

Illustrative rhodium-bisphosphite complex catalysts employable in such hydroformylation reactions encompassed by this invention may include those disclosed in the above mentioned patents and applications wherein the bisphosphite ligand is a ligand selected from the class consisting of Formulas (I) and (II) above. In general, such catalysts may be preformed, or formed in situ. as described e.g., in said U.S. Pat. Nos. 4,668,651 and 4,769,498, and consist essentially of rhodium in complex combination with the organobisphosphite ligand. It is believed that carbon monoxide is also present and complexed with the rhodium in the active species. The active catalyst species may also contain hydrogen directly bonded to the rhodium.

As noted above illustrative organobisphosphite ligands that may be employed as the bisphosphite ligand complexed to the rhodium catalyst and/or any free bisphosphite ligand (i.e. ligand that is not complexed with the rhodium metal in the active complex catalyst) in such hydroformylation reactions encompassed by this invention include those of Formulas (I) and (II) above.

Illustrative divalent radicals represented by X in the above bisphosphite formulas (I) and (II) include substituted and unsubstituted radicals selected from the group consisting of alkylene, alkylene-oxy-alkylene, phenylene, naphthylene, phenylene-(Q)$_n$-phenylene and naphthylene-(Q)$_n$-naphthylene radicals, and where Q, and n are the same as defined above. More specific illustrative divalent radicals represented by X include e.g. straight or branched chain alkylene radicals having from 2 to 18 (preferably 2 to 12) carbon atoms, e.g. ethylene, propylene, butylene, hexylene, dodecylene, octadecylene, 1,2,6- hexylene, and the like; —CH$_2$CH$_2$OCH$_2$CH$_2$—, 1,4-phenylene, 2,3-phenylene, 1,3,5-phenylene, 1,3-phenylene, 1,4-naphthylene, 1,5-naphthylene, 1,8-naphthylene, 2,3-naphthylene, 1,1'biphenyl- 2,2'-diyl, 1,1'-biphenyl- 4,4'-diyl, 1,1'binaphthyl-2,2'-diyl, 2,2'-binaphthyl- 1,1'-diyl, phenylene-CH$_2$-phenylene, phenylene-CH(CH$_3$)-phenylene radicals, and the like.

Illustrative radicals represented by Z$^1$ and Z$^2$, as well as possible substituent groups that may be present on the radicals represented by X in above Formulas (I) and (II), in addition to hydrogen, include any of those organic substituents containing from 1 to 18 carbon atoms, disclosed in U.S. Pat. No. 4,668,651, or any other radical that does not unduly adversely effect the process of this invention. Illustrative radicals and substituents encompass alkyl radicals, including primary, secondary and tertiary alkyl radicals such as methyl, ethyl n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy —OCH$_2$H$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; thionyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

More preferably X in Formulas (I) and (II) above represents a -phenylene-(Q)$_n$-phenylene radical having the formula

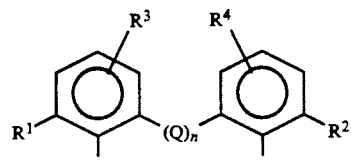

wherein each R$^1$, R$^2$, R$^3$ and R$^4$ individually represents hydrogen or an organic substituent radical containing from 1 to 18 carbon atoms, and wherein Q and n are the same as defined above. Illustrative types of such substituent radicals represented by R$^1$, R$^2$, R$^3$ and R$^4$ include those illustrated and discussed above as representing Z$^1$ and Z$^2$ or the substituent groups of X of Formulas (I) and (II).

Accordingly a preferred class of bisphosphite ligands employable in this invention are those of the following formulas:

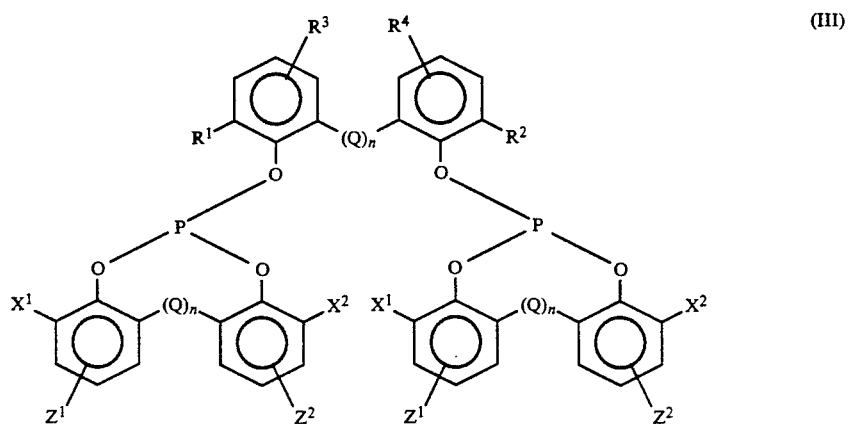

(III)

and

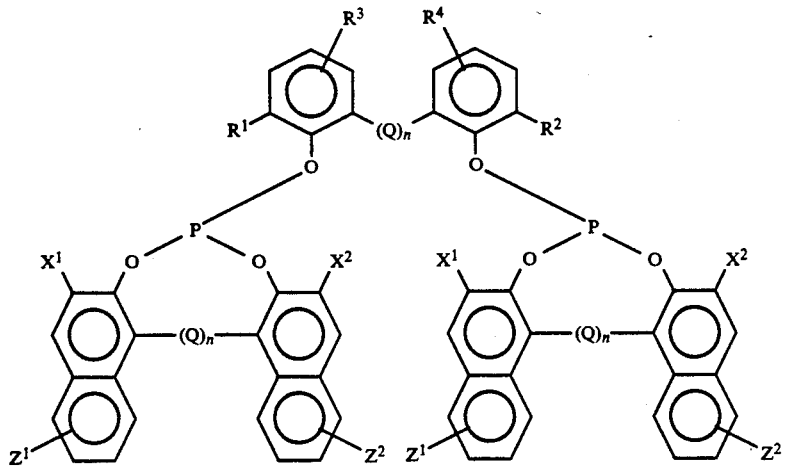

(IV)

wherein $X^1$, $X^2$, $Z^1$, $Z^2$, $R^1$, $R^2$, $R^3$, $R^4$ Q and n are the same as defined above.

It is of course to be understood that each $X^1$ and $X^2$ group, and each $Z^1$ and $Z^2$ group, and each $R^1$, $R^2$, $R^3$, and $R^4$ group in any of the given formulas may be the same or different. Moreover, while $Z^1$ and $Z^2$ of Formulas (I) and (II) and $R^3$ and $R^4$ of the above formulas may be present in the 4, 5 or 6 position of their respective phenyl radicals, preferably they are in the 5 position, i.e. in the para position to the oxygen atom attached to their respective phenyl radicals. Likewise while $Z^1$ and $Z^2$ of Formulas (II) and (IV) may be present in the 5, 6, 7 or 8 position of their respective naphthyl radicals, preferable they are in the 6 position of their respective naphthyl radicals, as shown in Formula (VI) below. Moreover, preferable $X^1$ is the same as $X^2$, and $Z^1$ is the same as $Z^2$, and $R^1$ is the same as $R^2$, and $R^3$ is the same as $R^4$ in any given bisphosphite ligand compound.

A more preferred class of bisphosphite ligands employable in this invention are those of the formulas

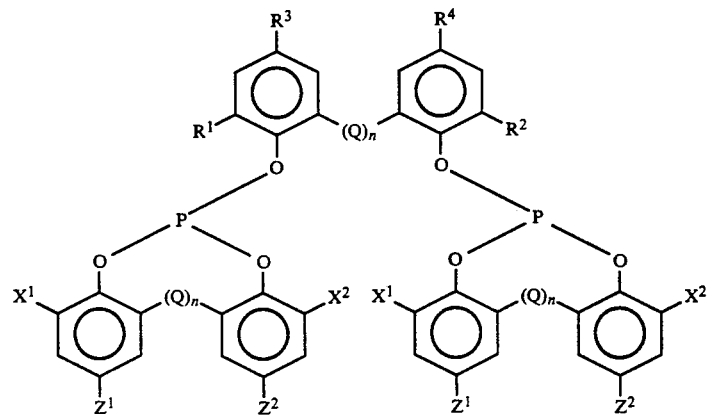

(V)

and

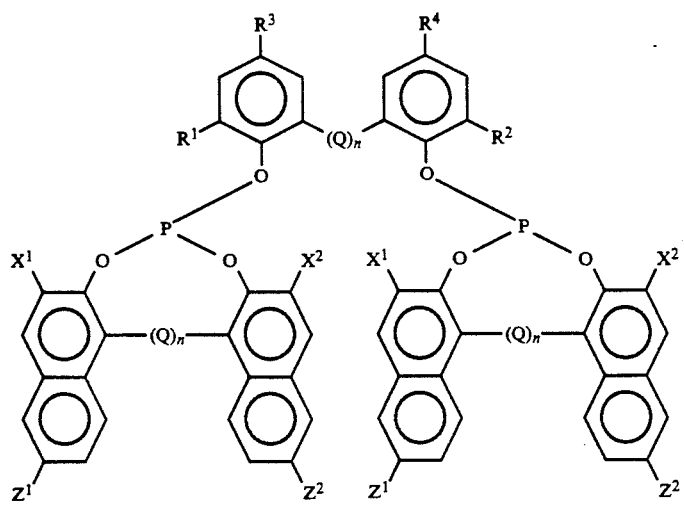

wherein $X^1$, $X^2$, $Z^1$, $Z^2$, $R^1$, $R^2$, $R^3$, $R^4$, Q and n are the same as defined above.

More preferably each $Z^1$, $Z^2$, $R^1$, $R^2$, $R^3$ and $R^4$ radical in any of the above formulas individually represents a radical selected from the group consisting of hydrogen, an alkyl radical having from 1 to 8 carbon atoms, phenyl, benzyl, cyclohexyl, 1-methylcyclohexyl, hydroxy and an alkoxy radical having from 1 to 8 carbon atoms, especially methoxy, while each n preferably is zero. Most preferably each $X^1$, $X^2$, $Z^1$ and $Z^2$ in any of the above formulas represents hydrogen, while each $R^1$ and $R^2$ in any of the above formulas individually represents a radical having a steric hindrance of isopropyl or greater, e.g. branched alkyl radicals of 3 to 8 carbon atoms, such as, isopropyl, t-butyl, t-amyl, iso-octyl and the like, especially tertiary butyl, and alicyclic radicals such as cyclohexyl and 1-methylcyclohexyl. Moreover, most preferably $R^1$ and $R^2$ are the same, and $R^3$ and $R^4$ are the same.

Specific illustrative examples of the bisphosphite ligands employable in this invention include such preferred ligands as 6,6'-[[3,3,'-bis(1,1-dimethylethyl)-5,5'-dimethoxy [1,1'biphenyl]-2,2'-diyl]bis (oxy)]bis-dibenzo[d,f] [1,3,2]dioxaphosphepin ligand having the formula

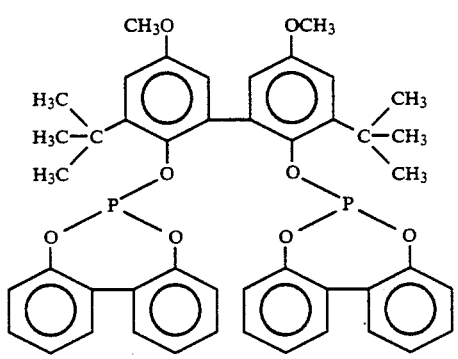

6,6'-[[3,3', 5,5'-tetrakis(1,1-dimethylpropyl) 1,1'-biphenyl-2,2'-diyl]bis(oxy)bis-dibenzo[d,f] [1,3,2]-dioxaphosphepin ligand having the formula

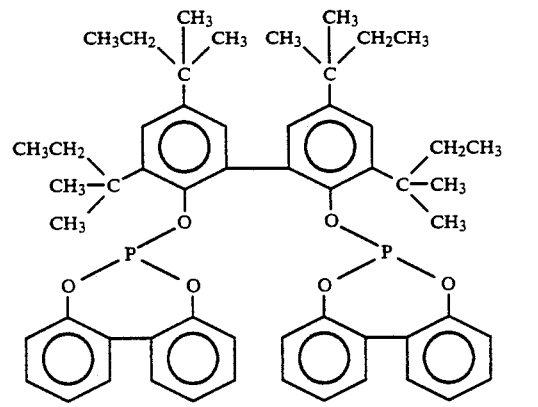

6,6'-[[3,3',5,5'-tetrakis(1,1-dimethylethyl) 1,1'-biphenyl-2,2'-diyl]bis(oxy)]bis-dibenzo[d,f] [1,3,2]-dioxaphosphepin ligand having the formula

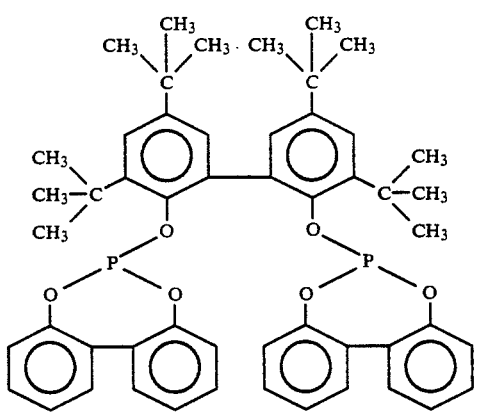

and the like. Additional exemplitive ligands include those of Formulas (V) and (VI) above having the substitutents listed in the following TABLES wherein
H represents Hydrogen
Me represents Methyl
Pr represents Propyl
t-Bu represents t-butyl
t-Am represents t-Amyl
Neo—P represents Neo—Pentyl t-He represents t-Hexyl [—C(CH$_3$)$_2$CH(CH$_3$)CH$_3$]
OMe represents Methoxy
OPr represents Propoxy

TABLE

[Illustrative Compounds of Formula (V)]

| Ref. No. | R$^1$ | R$^2$ | R$^3$ | R$^4$ | X$^1$ | X$^2$ | Z$^1$ | Z$^2$ | Q | n |
|---|---|---|---|---|---|---|---|---|---|---|
| 1. | t-Bu | t-Bu | t-Bu | t-Bu | Me | Me | H | H | — | 0 |
| 2. | t-Bu | t-Bu | t-Bu | t-Bu | Me | H | H | H | — | 0 |
| 3. | t-Bu | t-Bu | t-Bu | t-Bu | H | Pr | H | H | — | 0 |
| 4. | t-Bu | t-Bu | t-Bu | t-Bu | H | H | H | H | —CH$_2$— | 1 |
| 5. | t-Bu | t-Bu | t-Bu | t-Bu | H | H | H | H | —CH(CH$_3$)— | 1 |
| 6. | t-Bu | t-Bu | t-Bu | t-Bu | H | H | Me | Me | — | 0 |
| 7. | t-Bu | t-Bu | t-Bu | t-Bu | H | H | Pr | Pr | — | 0 |
| 8. | t-Bu | t-Bu | t-Bu | t-Bu | H | H | OMe | OMe | — | 0 |
| 9. | t-Bu | t-Bu | t-Bu | t-Bu | H | H | OPr | OPr | — | 0 |
| 10. | t-Bu | t-Bu | t-Bu | t-Bu | H | H | t-Bu | t-Bu | — | 0 |
| 11. | t-Bu | t-Bu | H | H | H | H | H | H | — | 0 |
| 12. | t-Am | t-Am | t-Am | t-Am | H | H | OMe | OMe | — | 0 |
| 13. | t-Am | t-Am | OMe | OMe | H | H | H | H | — | 0 |
| 14. | t-Am | t-Am | t-Bu | t-Bu | H | H | H | H | — | 0 |
| 15. | t-Am | t-Am | H | H | H | H | H | H | — | 0 |
| 16. | Neo-P | Neo-P | Neo-P | Neo-P | H | H | H | H | — | 0 |
| 17. | Neo-P | Neo-P | H | H | H | H | H | H | — | 0 |
| 18. | t-He | t-He | t-He | t-He | H | H | H | H | — | 0 |
| 19. | t-He | t-He | H | H | H | H | H | H | — | 0 |
| 20. | t-He | t-He | OMe | OMe | H | H | H | H | — | 0 |
| 21. | t-He | t-He | t-Bu | t-Bu | H | H | H | H | — | 0 |

TABLE

[Illustrative Compounds of Formula VI)]

| Ref. No. | R$^1$ | R$^2$ | R$^3$ | R$^4$ | X$^1$ | X$^2$ | Z$^1$ | Z$^2$ | Q | n |
|---|---|---|---|---|---|---|---|---|---|---|
| 1. | t-Bu | t-Bu | t-Bu | t-Bu | H | H | H | H | — | 0 |
| 2. | t-Am | t-Am | t-Am | t-Am | H | H | H | H | — | 0 |
| 3. | t-He | t-He | t-He | t-He | H | H | H | H | — | 0 |
| 4. | t-Bu | t-Bu | OMe | OMe | H | H | H | H | — | 0 |
| 5. | t-Am | t-Am | OMe | OMe | Me | H | OMe | OMe | — | 0 |
| 6. | t-Bu | t-Bu | H | H | H | H | OMe | OMe | —CH$_2$— | 1 |
| 7. | t-Bu | t-Bu | H | H | Pr | H | H | H | — | 0 |
| 8. | Neo-P | Neo-P | Neo-P | Neo-P | H | H | H | H | — | 0 |
| 9. | t-Am | t-Am | t-Bu | t-Bu | H | H | H | H | — | 0 |
| 10. | t-He | t-He | H | H | H | H | H | H | — | 0 |
| 11. | t-Bu | t-Bu | H | H | H | H | H | H | — | 0 |
| 12. | t-Am | t-Am | H | H | H | H | H | H | — | 0 |

Such types of bisphosphite ligands employable in this invention and/or methods for their preparation are well known as seen disclosed for example in U.S. Pat. No. 4,668,651. For instance, the bisphosphite ligands can be readily and easily prepared via a series of conventional phosphorus halide-alcohol condensation reactions that are well known in the art. A simple method for preparing such ligands may comprise (a) reacting a corresponding organic diphenolic compound with phosphorus trichloride to form the corresponding organic phosphorochloridite intermediate, (b) reacting said intermediate with a diol (corresponding to X in the above formulas) to form the corresponding hydroxy substituted diorganophosphite intermediate, (c) reacting said diorganophosphite intermediate with phosphorus trichloride to form the corresponding phosphorodichloridite intermediate and (d) reacting said dichloridite with a corresponding diol to arrive at the corresponding desired bisphosphite ligand. Such condensation reactions are preferably carried out in the presence of a solvent, e.g. toluene, and an HCl acceptor, e.g. an amine, and may be carried out in a single-pot synthesis, if desired. For instance, desired symmetrical phosphite type ligands, such as encompassed e.g. by Formulas V and VI above, can be directly produced by reacting two mole equivalents of the phosphorochloridite intermediate of Step (a) above with one mole equivalent of the diol corresponding to X. Moreover, the bisphosphite ligands employable herein can be readily identified and characterized by conventional analytical techniques, such as e.g. Phosphorus-31 nuclear magnetic resonance spectroscopy and Fast Atom Bombardment Mass Spectroscopy if desired.

As noted above the hydroformylation reaction conditions that may be employed in the hydroformylation processes encompassed by this invention may include any suitable continuous hydroformylation conditions heretofore disclosed in the above-mentioned patents. For instance, the total gas pressure of hydrogen, carbon monoxide and olefinic unsaturated starting compound of the hydroformylation process may range from about 1 to about 10,000 psia. In general, however, it is preferred that the process be operated at a total gas pressure of hydrogen, carbon monoxide and olefinic unsaturated starting compound of less than about 1500 psia and more preferably less than about 500 psia. The minimum total pressure being limited predominately by the amount of reactants necessary to obtain a desired rate of reaction. More specifically the carbon monoxide partial pressure of the hydroformylation process of this invention is preferable from about 1 to about 120 psia, and more preferably from about 3 to about 90 psia, while the hydrogen partial pressure is preferably about 15 to about 160 psia and more preferably from about 30 to about 100 psia. In general H$_2$:CO molar ratio of gaseous hydrogen to carbon monoxide may range from about 1:10 to 100:1 or higher, the more preferred hydrogen to carbon monoxide molar ratio being from about 1:1 to about 10:1. Further, the hydroformylation process may be conducted at a reaction temperature from about 45° C. to about 150°. In general hydroformylation reaction temperature of about 50° C. to about 120° are preferred for all types of olefinic starting materials, the more preferred reaction temperatures being from about 50° C. to about 100° C. and most preferably about 80° C..

The olefinic starting material reactants that may be employed in the hydroformylation reactions encompassed by this invention include olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isobutene, etc., (such as so called dimeric, trimeric or tetrameric propylene, and the like, as disclosed, e.g., in U.S. Pat. Nos. 4,518,809 and 4,528,403). Moreover, such olefinic compounds may further contain one or more ethylenic unsaturated groups, and of course, mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described, e.g., in U.S. Pat. Nos. 3,527,809; 4,668,651 and the like.

Illustrative olefinic unsaturated compounds are alpha-olefins, internal olefins, alkyl alkenoates, alkenyl alkanoates, alkenyl alkyl ethers, alkenols, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, betapinene, dicyclopentadiene, cyclooctadiene, camphene, linalool, and the like.

Of course, it is understood that mixtures of different olefinic starting materials can be employed, if desired, by the hydroformylation process of the subject invention. More preferably the subject invention is especially useful for the production of aldehydes, by hydroformylating alpha olefins containing from 2 to 20 carbon atoms, including isobutylene, and internal olefins containing from 4 to 20 carbon atoms as well as starting material mixtures of such alpha olefins and internal olefins. It is also to be understood that commercial alpha olefins containing 4 or more carbon atoms may contain minor amounts of corresponding internal olefins and/or their corresponding saturated hydrocarbons and that such commercial olefins need not necessarily be purified from same prior to being hydroformylated.

As noted above, the continuous hydroformylation process of this invention involved the use of a rhodium-bisphosphite ligand complex catalyst as described herein. Of course mixtures of such catalysts can also be employed if desired. The amount of rhodium-phosphite complex catalyst present in the reaction medium of a given hydroformylation process encompassed by this invention need only be that minimum amount necessary to provide the given rhodium concentration desired to be employed and which will furnish the basis for at least the catalytic amount of rhodium necessary to catalyze the particular hydroformylation process involved such as disclosed e.g. in the above-mentioned patents. In general, rhodium concentrations in the range of from about 10 ppm to about 1000 ppm, calculated as free rhodium, in the hydroformylation reaction medium should be sufficient for most processes, while it is generrally preferred to employ from about 10 to 500 ppm of rhodium and more preferably from 25 to 350 ppm to rhodium.

In addition to the rhodium-bisphosphite ligand complex catalyst the hydroformylation process encompassed by this invention may be carried out in the presence of free bisphosphite ligand, i.e. ligand that is not complexed with the rhodium metal of the complex catalyst employed. Said free bisphosphite ligand may correspond to any of the above defined bisphosphite ligands discussed above as employable herein. When employed it is preferred that the free bisphosphite ligand be the same as the bisphosphite ligand of the rhodium-bisphosphite complex catalyst employed. However, such ligands need not be the same in any given process. Moreover, while it may not be absolutely necessary for the hydroformylation process to be carried out in the presence of any such free bisphosphite ligand, the presence of at least some amount of free bisphosphite ligand in the hydroformylation reaction medium is preferred. Thus the hydroformylation process of this invention may be carried out in the absence or presence of any amount of free bisphosphite ligand, e.g. up to 100 moles, or higher per mole of rhodium metal in the hydroformylation reaction medium. Preferably the hydroformylation process of this invention is carried out in the presence of from about 1 to about 50 moles of bisphosphite ligand, and more preferably from about 1 to about 4 moles of bisphosphite ligand, per mole of rhodium metal present in the reaction medium; said amounts of bisphosphite ligand being the sum of both the amount of bisphosphite ligand that is bound (complexed) to the rhodium metal present and the amount of free (non-complexed) bisphosphite ligand present. Of course, if desired, make-up or additional bisphosphite ligand can be supplied to the reaction medium of the hydroformylation process at any time and in any suitable manner, e.g. to maintain a predetermined level of free ligand in the reaction medium.

The hydroformylation reactions encompassed by this invention are also conducted in the presence of an organic solvent for the rhodium-bisphosphite complex catalyst and any free bisphosphite ligand that might be present. Any suitable solvent which does not unduly adversely interfere with the intended hydroformylation process can be employed. Illustrative suitable solvents for rhodium catalyzed hydroformylation processes include those disclosed e.g. in U.S. Pat. No. 4,668,651. Of course mixtures of one or more different solvents may be employed if desired. Most preferably the solvent will be one in which the olefinic starting material, catalyst, and weakly acidic additive if employed, are all substantially soluble. In general, it is preferred to employ aldehyde compounds corresponding to the aldehyde products desired to be produced and/or higher boiling aldehyde liquid condensation by-products as the primary solvent, such as the higher boiling aldehyde liquid condensation by-products that are produced in situ during the hydroformylation process. Indeed, while one may employ any suitable solvent at the start up of a continuous process, the primary solvent will normally eventually comprise both aldehyde products and higher boiling aldehyde liquid condensation by-products due to the nature of such continuous processes. Such aldehyde condensation by-products can also be preformed if desired and used accordingly. Of course, the amount of solvent employed is not critical to the subject invention and need only be that amount sufficient to provide the reaction medium with the particular rhodium concentration desired for a given process. In general, the amount of solvent may range from about 5 percent by weight up to about 95 percent by weight or more based on the total weight of the reaction medium.

Moreover as noted herein, the solubilized rhodium-phosphite complex catalyzed continuous hydroformylation process employable in this invention preferably involves a liquid catalyst recycle procedure. Such types of liquid catalyst recycle procedures are known as seen disclosed e.g. in U.S. Pat. Nos. 4,668,651; 4,774,361; 5,102,505 and 5,110,990, and thus need not be particularly detailed herein, since any such conventional catalyst recycle procedures may be employed by this invention. For instance, in such liquid catalyst recycle procedures it is common place to continuously remove a portion of the liquid reaction product medium, containing e.g. the aldehyde product, the solubilized rhodium-bisphosphite complex catalyst, free bisphosphite ligand, and organic solvent, as well as by-products produced in situ by the hydroformylation, e.g. aldehyde condensation by-products etc., and unreacted olefinic starting material, carbon monoxide and hydrogen (syn gas) dissolved in said medium, from the hydroformylation reactor, to a distillation zone, e.g. a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains rhodium-bisphosphite complex catalyst, solvent, free bisphosphite ligand and usually some undistilled aldehyde product is then recycled back, with or without further treatment as desired, along with whatever by-product and non-volatilized gaseous reactants that might still also be dissolved in said recycled liquid residue, in any conventional manner desired, to the hydroformylation reactor, such as disclosed e.g. in the above-mentioned patents. Moreover the reactant gases so removed by such distillation from the vaporizer may also be recycled back to the reactor if desired.

The distillation and separation of the desired aldehyde product from the rhodium-bisphosphite complex catalyst containing product solution may take place at any suitable temperature desired. In general it is recommended that such distillation take place at low temperatures, such as below 150° C., and more preferably at a temperature in the range of from about 50° C. to about 130° C., and most preferably up to about 115° C. It is also generally recommended that such aldehyde distillation take place under reduced pressure, e.g. a total gas pressure that is substantially lower than the total gas pressure employed during hydroformylation when low boiling aldehydes (e.g. $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium and then pass said volatilized gases and liquid medium which now contains a much lower syn gas concentration than was present in the hydroformylation reaction medium to the distillation zone e.g. vaporizer/separator, wherein the desired aldehyde product is distilled. In general distillation pressures ranging from vacuum pressures or below on up to total gas pressure of about 50 psig should be sufficient for most purposes.

As stated above, the subject invention resides in the discovery that intrinsic deactivation of such rhodium-bisphosphite complex catalysts as discussed herein, can be reversed or at least minimized by carrying out the hydroformylation process in the added presence of a minor amount of a catalytic activity enhancing additive present in the hydroformylation reaction medium of the process, said additive being selected from the class consisting of added water, a weakly acidic compound, or both added water and a weakly acidic compound. Said minor amount of catalytic activity enhancing additive (i.e. that amount of added water and/or said weakly acidic compound additive) in the hydroformylation reaction medium of the process of this invention may range from about 0.05 to about 20 weight percent or higher if desired, based on the total weight of the hydroformylation reaction medium, and more preferably from about 0.05 to 15 weight percent. Moreover while the process of this invention may be carried out in the absence of any added water or in the absence of any weakly acidic additive, it is to understand that the hydroformylation process of this invention involves the employment of at least some amount of added water and/or said weakly acidic compound additive as discussed herein.

Without wishing to be bound to any exact theory or mechanistic discourse, it appears that the structural features of certain bisphosphite ligands which make them such beneficially unique hydroformylation catalyst promoters, as discussed e.g. in U.S. Pat. No. 4,668,651, are also a cause of the intrinsic catalyst deactivation discussed herein.

For instance while bisphosphite promoted rhodium hydroformylation catalysts of the type employable herein have been found to be highly active and selective in converting terminal as well as internal olefins to aldehydes, it has also been observed that such catalyst systems undergo a loss in catalytic activity over time. In the course of studying such catalysts, the formation of a class of diorganophosphite by-products have been discovered which can best be described as monophosphite decomposition products of the bisphosphite ligand employed. Such evidence is consistent with the view that the bisphosphite reacts with an alcohol or an alkoxy radical, such as likely to arise from the reaction of the aldehyde product and hydrogen (or hydride), to form an alkyl [1,1'-biaryl-2,2'-diyl] phosphite, i.e. a monophosphite by-product, which may be further identifiable and characterizable by conventional analytical techniques, such as Phosphorus-31 nuclear magnetic resonance spectroscopy and Fast Atom Bombardment Mass Spectroscopy, if desired. The intrinsic catalyst deactivation of the preferred rhodium-bisphosphite ligand complex catalyst is thus believed to be primarily caused by such monophosphite by-product which acts as a catalyst poison by competing for coordination sites on the rhodium metal and forming complexes that are far less catalytically reactive than the preferred rhodium-bisphosphite ligand complex catalyst employed.

A means for reversing or greatly minimizing such intrinsic catalyst deactivation has now been discovered which comprises carrying out the hydroformylation process in the presence of added water and/or certain weakly acidic additives as disclosed herein.

For instance, heretofore conventional rhodium-bisphosphite complex catalyzed continuous hydroformylation processes have been carried out in a non-aqueous organic hydroformylation reaction medium, which is to say that the processes were conducted in the absence or essential absence of any deliberately added water. Any water, if present at all, in such hydroformylation reaction mediums was present only as the result of possible trace amounts in the reactants (e.g. syn gas) employed or as a result of in situ formation (e.g. the possible condensation reaction of aldehyde product and its dimer by-product) and not present in any amount sufficient to unduly adversely affect the performance of the catalyst or cause undue degradation (hydrolysis) of the bisphosphite ligand, or cause any significant hydrolysis of the undesirable monophosphite ligand by-product.

It has now been discovered that the catalyst activity of a rhodium-bisphosphite ligand complex catalyst that has become at least partially intrinsically deactivated due to the formation of monophosphite ligand by-product over continuous hydroformylation, can be restored to a significant degree (i.e. catalyst reactivation) by adding water and/or a weakly acidic additive as described herein to the reaction medium of the hydroformylation process. More preferably such intrinsic catalyst deactivation can be prevented or at least greatly minimized by adding water and/or a weakly acidic additive to the reaction medium prior to any significant build-up of such monophosphite by-products (e.g. employing such added water and/or weakly acidic additive in the reaction medium from the start of the hydroformylation process).

By way of further explanation it has been surprisingly found that water causes the undesirable monophosphite ligand by-product to hydrolyze at a much faster rate than the desired bisphosphite ligand employed and that such selective hydrolysis can be catalyzed or enhanced by the use of certain weakly acidic additives as described herein. Such a discovery allows one to selectively remove such undesired monophosphite from the reaction system or more preferably prevent or minimize any undue adverse buildup of such monophosphite ligand within the reaction system.

Weakly acidic additives which are employable herein and which are added to the hydroformylation reaction medium are well known compounds as are methods for their preparation and in general are readily commercially available. Any weakly acidic compound having a pKa value of from about 1.0 to about 12 and more preferably from about 2.5 to about 10 may be employed herein. The slightly acidic nature of such compounds has been found to catalyze the hydrolysis of the monophosphite ligand by-product, even when no additional water is deliberately added to the hydroformylation reaction medium, without unduly adversely affecting the bisphosphite ligand employed. For example, the acidity of the additive compound should not be so high as to also destroy the bisphosphite ligand by acid hydrolysis at an unacceptable rate. Such pKa values are a measure of the acidity of a compound as given in terms of the negative (decadic) logarithm of the acidic dissociation constant, i.e. $-\log_{10} Ka = pKa$ as defined in "Lange's Handbook of Chemistry", Thirteenth Edition, J. A. Dean Editor, pp 5–18 to 5–60 (1985); McGraw-Hill Book Company. Of course estimated (est.) pKa values may be obtained by making a comparison with compounds of recognizably similar character for which pKa values are known as discussed on page 5–13 of said "Lange's Handbook of Chemistry". Among the more preferred weakly acidic compounds are aryl compounds containing from 1 to 3 substituent radicals directly bonded thereto (i.e. directly attached to the aryl ring of said aryl compounds as opposed to being bonded to some substituent of said aryl compounds), each said substituent radical being individually selected from the group consisting of hydroxy and carboxylic acid radicals. Such aryl compounds include those selected from the group consisting of phenyl, biphenyl, naphthyl and dinaphthyl compounds as well as heterocyclic type aryl compounds such as pyridine, and the like. Preferably such weakly acidic compounds contain from 1 to 2 hydroxy radicals or 1 to 2 carboxylic acid radicals or mixtures thereof. Of course, if desired such weakly acidic aryl compounds may also contain other groups or substituents which do not unduly adversely interfere with the purpose of this invention, such as alkyl, halide, trifluoromethyl, nitro, and alkoxy radicals, and the like.

Illustrative preferred hydroxy substituted and carboxylic acid substituted aryl radicals along with their pKa values in parenthesis include, e.g.

| Weakly Acidic Compound | pka Values |
|---|---|
| Biphenol (2,2'-dihydroxybiphenyl) | (9.0) |
| 2-hydroxybiphenyl (2-phenylphenol) | (9.55) |
| 4-hydroxybiphenyl (4-phenylphenol) | (9.55) |
| 2,2'-dinaphthol (2,2'-dihydroxybinaphthyl) | (9.2 est.) |
| 4-4'-dimethoxy-2,2'-dihydroxybiphenyl | (7.5 est.) |
| 4-4'-di-t-butyl-2,2'-dihydroxybiphenyl | (9.5 est.) |
| 4-4'-dibromo-2,2'-dihydroxybiphenyl | (7.5 est.) |
| Catechol (1,2-dihydroxybenzene) | (9.36) |
| 3-trifluoromethylphenol | (8.95) |
| 3,5-bis (trifluoromethyl) phenol | (8.0 est.) |
| 4-chlorophenol | (9.43) |
| 2,4-dichlorophenol | (7.85) |
| 3,5-dichlorophenol | (8.18) |
| 4-nitrophenol | (7.15) |
| benzoic acid | (4.20) |
| Salicylic acid (2-hydroxy benzoic acid) | (2.98) |
| 4-ethoxybenzoic acid | (4.8) |
| 4-trifluoromethylbenzoic acid | (4.0 est.) |
| 4-nitrobenzoic acid | (3.44) |
| 4-t-butylbenzoic acid | (4.39) |
| picolinic acid | (5.29) |
| 3,5-dihydroxybenzoic acid | (4.04) |
| 3,5-dimethoxybenzoic acid | (4.0 est.) |
| Phthalic acid (1,2-dicarboxylic acid phenyl) | (2.95) |
| Isophthalic acid (1,3-dicarboxylic acid phenyl) | (3.54) |

When selecting a particular weakly acidic compound for use in a given process of this invention, in addition to the pKa value of the weakly acidic compound, one may also wish to consider its overall catalytic performance in conjunction with the many particulars of the hydroformylation process involved, e.g. the particular olefin to be hydroformylated, the particular aldehyde product and aldehyde product isomer ratio desired, the bisphosphite ligand employed, the amount of water present in the reaction medium, the amount of monophosphite ligand present in the reaction medium, and the like, as well as such characteristics of the weakly acidic compound additive as its solubility in the hydroformylation reaction medium and its volatility (e.g. boiling point), etc.

Of course it is to be understood that such weakly acidic compound additives may be employed individually or as mixtures of two or more different weakly acidic compounds. Moreover the amount of such weakly acidic compound additives employable in any given process of this invention need only be a catalytic amount i.e. that minimum amount necessary to catalyze the selective hydrolysis of the monophosphite ligand by-product. Amounts of such weakly acidic compound additives of from 0 to about 20 weight percent or higher if desired, based on the total weight of the hydroformylation reaction medium may be employed. In general, when employed, it is preferred to employ amounts of such weakly acidic compound additives in the range of from about 0.1 to about 5.0 weight percent based on the total weight of the hydroformylation reaction medium. More preferably the hydroformylation process of this invention is carried out in the absence of any such weakly acidic compound additives. Indeed it has been further surprising discovered that merely by deliberately providing the hydroformylation reaction medium with a small amount of added water one can selectively hydrolyze the undesirable monophosphite ligand by-product at a suitably acceptable rate without unduly adversely hydrolyzing the desired bisphosphite ligand employed. For instance, by providing the hydroformylation reaction medium of the process of this invention with a suitable amount of added water right from the start of the hydroformylation process (or at least before any undue adverse build-up of monophosphite ligand by-product has taken place) one can selectively hydrolyze (without the need of any weakly acidic compound additive) the undesirable monophosphite ligand by-product as it being formed in situ and thereby prevent or minimize any undue adverse build-up of said monophosphite ligand. Such selective hydrolysis in turn prevents or minimizes the intrinsic rhodium-bisphosphite ligand complex catalyst deactivation caused by such monophosphite ligand as previously discussed herein.

The term "added water" as employed herein refers to water that has been deliberately supplied to the hydroformylation reaction system (as opposed to the presence of only in situ produced water in the hydroformylation reaction medium) of the subject invention. As noted above it may not be necessary to employ any such added water in the process of the subject invention, since hydrolysis of the monophosphite ligand by-product, due to the presence of only in situ produced water in the reaction medium, may be satisfactorily catalyzed by the use of a weakly acidic compound additive provided that the amount of monophosphite ligand present is not too great. Thus, it is preferred to carry out the hydroformylation process of the subject invention in the presence of a suitable amount of added water regardless of whether a weakly acidic compound additive is also employed. Accordingly, the amount of such added water employable in any given process of this invention need only be that minimum amount necessary to achieve the desired selective hydrolysis of the monophosphite ligand by-product. Amounts of such added water of from 0 to about 20 weight percent, or higher if desired, based on the total weight of the hydroformylation reaction medium may be employed. Of course amounts of added water that might also lead to adversely hydrolyzing the desired bisphosphite ligand at an undesirable rate or result in a two phase (organic-aqueous) hydroformylation reaction medium as opposed to the desired and conventional single phase (organic) homogeneous hydroformylation reaction medium are to be avoided. In general, when employed, it is preferred to employ amounts of such added water in the range of from about 0.05 to about 10 weight percent based on the total weight of the hydroformylation reaction medium.

The addition of the added water and/or weakly acidic compound additives to the hydroformylation reaction medium of this invention may be accomplished in any suitable manner desired and their order of addition is immaterial. For instance they may be added separately and/or simultaneously, or premixed and then added if desired. Moreover, they may be introduced into the reaction system on their own or along with any conventional reactant, e.g. along with the syn gas or olefin reactant, or via the catalyst recycle line. As noted it is preferred to employ such added water and/or weakly acidic compound additive (when indeed such is used) right from the start-up of the hydroformylation process. For example the weakly acidic compound additive may be solubilized in the rhodium catalyst precursor composition and added to the reactor along with said composition, while water may be preferably added to the reaction medium via water saturated syn gas, obtained e.g., by sparging syn gas through a container of water prior to introducing the syn gas into the reactor. Thus an additional benefit of the subject invention is that conventional rhodium catalyzed continuous hydroformylation reaction systems do not have to be significantly modified, if indeed they have to be modified at all, to accommodate the subject invention. The selective hydrolysis of the undesired monophosphite ligand by-product can take place in the same hydroformylation reactor and throughout the continuous reaction system and under the same hydroformylation conditions employed to produce the desired aldehyde product from its olefinic starting material. Thus the conditions employed to effect the selective hydrolysis of the undesirable monophosphite ligand by-product are not critical and include any of the same conventional continuous hydroformylation conditions heretofore employed in the art. Such desired flexibility furnishes one with wide processing latitude for controlling and balancing the degree of improvement desired in preventing or minimizing the intrinsic deactivation of the rhodium-bisphosphite ligand complex catalyst caused by the monophosphite ligand by-product.

Hydrolysis of the monophosphite ligand by-product in turn leads to the formation of hydroxy alkyl phosphonic acid as outlined e.g. in U.S. Pat. No. 4,737,588. Moreover such hydroxy alkyl phosphonic acids are also undesirable in rhodium-organophosphite catalyzed hydroformylation processes as seen disclosed, e.g. in U.S. Pat. Nos. 4,737,588 and 4,769,498. However the formation of such hydroxy alkyl phosphonic acid as a result of the hydrolysis of the monophosphite ligand by-product via the subject invention, is none the less, preferable to the continued presence of the more undesirable monophosphite ligand by-product in the hydroformylation process. Indeed it is considered that the presence of such hydroxy alkyl phosphonic acid by-product may be effectively controlled as described in said U.S. Pat. Nos. 4,737,588 and 4,769,498. For instance the liquid reaction effluent stream of the subject continuous liquid recycle process may be passed, either prior to or more preferably after separation of the aldehyde product therefrom, through any suitable weakly basic anion exchange resin, such as a bed of amine-Amberlyst ® resin, e.g. Amberlyst ®A-21, and the like, to remove some or all of the undesirable hydroxy alkyl phosphonic acid by-product that might be present in the liquid catalyst containing stream prior to its reincorporation into the hydroformylation reactor. Of course if desired, more than one such basic anion exchange resin bed, e.g. a series of such beds, may be employed and any such bed may be easily removed and/or replaced as required or desired. Alternatively if desired, any part or all of the hydroxy alkyl phosphonic acid contaminated catalyst recycle stream may be periodically removed from the continuous recycle operation and the contaminated liquid so removed treated in the same fashion as outlined above, to eliminate or reduce the amount of hydroxy alkyl phosphonic acid contained therein prior to reusing the catalyst containing liquid in the hydroformylation process. Likewise, any other suitable method for removing such hydroxy alkyl phosphonic acid by-product from the hydroformylation process of this invention may be employed herein if desired such as by extraction of the acid with a weak base, e.g. sodium bicarbonate.

A newer and more preferred method for minimizing and/or controlling the problem of such undesirable hydroxy alkyl phosphine acid by-product resides in the employment of certain epoxide reagents to scavenge or sequester such acids, as described, e.g., in assignee's copending U.S. patent application Ser. No. 953,014, entitled "Process For Stabilizing Phosphite Ligands", filed concurrently with this present application, the entire disclosure of which is encompassed herein by reference thereto. Accordingly, the hydroformylation process of this invention is also preferably carried out in the additional presence of such an epoxide reagent.

Illustrative epoxide reagents include, e.g. those having the formulas set forth below. The first such formula is as follows:

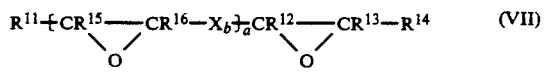 (VII)

wherein:
(1) a is 0 or 1;
(2) b is 0 or 1;
(3) $R^{11}$, $R^{12}$, $R^{13}$, $R^{14}$, $R^{15}$ and $R^{16}$ are independently selected from the group consisting of hydrogen; monovalent hydrocarbon radicals (such as alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$, $R^{12}$, $R^{13}$, $R^{14}$, $R^{15}$ and $R^{16}$ are linked together to form a cyclic structure which has up to about 30 carbon atoms and which may comprise a plurality of ring structures such as bicyclo-, tricyclo-, tetracyclo- and n-cyclo- groups;
(4) X is a divalent bridging group selected from the group consisting of substituted or unsubstituted alkylene, arylene, aralkylene, and alkarylene groups having up to about 30 carbon atoms, —O—, —S—, —NR$^{19}$—, —SiR$^{20}$R$^{21}$, and —CO—, and wherein each radical $R^{19}$, $R^{20}$, and $R^{21}$ individually represents H or alkyl groups.

In this definition, the word "substituted denotes presence of groups which do not react with epoxides, such as alkoxy and aryloxy groups. Excluded from the definition of "substituted" are halogens, carboxyl moieties, nitrile groups, and any other moieties which react with epoxides. Hydrocarbon epoxides generally are preferred.

When a equal 0 and b equal 0 in formula (VII) above, the epoxides may have the formula:

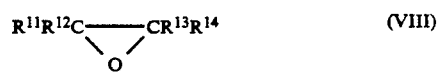 (VIII)

wherein $R^{11}$, $R^{12}$, $R^{13}$, and $R^{14}$ are as described above with regard to formula (VII). Examples of suitable epoxides of formula (VIII) include, but are not limited to, 1,2-cyclohexene oxide; styrene oxide; propylene oxide; 1,2-octene oxide; 1,2-decene oxide; 1,2-dodecene oxide; 1,2-hexadecene oxide; 1,2-octadecene oxide; ethylene oxide; 1,2-cyclododecene oxide; stilbene oxide; isobutylene oxide; 2,3-epoxybutane; 1,2-epoxybutane; 1,2-epoxyhexane; cyclopentene oxide; cyclooctene oxide; cyclodecene oxide; and 1,2-epoxy-3-phenoxy- propane. Preferably $R^{11}$ and $R^{12}$ in formula (VIII) are hydrogen.

Epoxy compositions of formula (VIII) above having at least one ring in a cyclic structure formed by the combination of one of $R^{11}$ and $R^{12}$ groups with one of $R^{13}$ and $R^{14}$ groups include cyclic structures which have a plurality of rings associated therewith, including bicyclo- and other n-cyclo- groups. Bicyclo-groups are cyclic hydrocarbon groups consisting of two rings only having two or more atoms in common. Tricyclo-, tetracyclo-, and other n-cyclo- compounds also are included within the definition of cyclic structures having a plurality of rings. Examples of such plural ring structures within the scope of a cyclic structure formed by the combination of one of $R^{11}$ and $R^{12}$ groups with one of $R^{13}$ and $R^{14}$ groups include the bicyclo- compounds norbornane which is also known as bicyclo[2.2.1] heptane and α-pinene which is also known as 2,7,7-trimethyl-Δ$^2$-bicyclo [1.1.3] heptene. Epoxy compounds suitable for use which are formed from norbornane and α-pinene are 2,3-epoxynorbornane which is also known as 2,3-epoxy-bicyclo[2.2.1]heptane) and α-pinene oxide.

Epoxy compounds of formula (VIII) above, wherein the $R^{11}$ and $R^{12}$ groups together or the $R^{13}$ and $R^{14}$ groups together, or both, may form cyclic structure(s) which may include a plurality of rings. The cyclic structure of such compounds can include bicyclo-, tricyclo-, and other n-cyclo compounds. Nopinene, which is also known as β-pinene or 7,7-dimethyl-2-methylenenorpinane, is a composition having a ring structure which yields a useful epoxy compound. The epoxy compound derived from nopinene, β-pinene oxide, is a compound of formula (VIII) above wherein $R^{11}$ and $R^{12}$ form a cyclic structure having a plurality of ring structures, $R^{13}$ is a methyl group, and $R^{14}$ is hydrogen.

Diepoxides also are useful. Suitable diepoxy compounds of formula (VIII) include 1,3-butadiene diepoxide, 1,2,7,8-diepoxyoctane, diepoxycyclooctane, dicyclopentadiene dioxide, and 3,4-epoxy cyclohexyl methyl-3,4-epoxy cyclohexyl carboxylate (available as ERL-4221 ®, a trademark of Union Carbide Chemicals and Plastics Technology Corporation).

The quantity of epoxide utilized in accordance with the process of this invention is that quantity sufficient to interact with the phosphorous acids which can cause degradation of phosphite ligand-containing catalysts. Preferably, the quantity of epoxide is sufficient to maintain the concentration of acidic by-products below the threshold level which causes rapid degradation of the ligand as disclosed, e.g., in assignee's above-mentioned U.S. patent application Ser. No. 953,015, entitled "Process For Stabilizing Phosphite Ligands", filed concurrently with this present application. This preferred quantity of epoxide is the quantity which ensures that any degradation of the ligand proceeds by the "non-catalytic mechanism" as described in "The Kinetic Rate Law for Autocatalytic Reactions" by Mata—Perez et al, Journal of Chemical Education, Vol. 64, No. 11 Nov. 1987, pages 925 to 927 rather that by the "catalytic mechanism" described in that article. Most preferably, the quantity is sufficient to maintain the concentration of acidic catalysts at an essentially undetectable level.

A suitable concentration of epoxide in a hydroformylation reaction mixture used in the present invention typically is at least about 0.001 weight percent of the total weight of reaction mixture. Typically, the maximum epoxide concentration is limited by practical considerations, such as the cost of epoxide and by the undesirable side effects of too much epoxide (e.g., the formation of acetal and polyether byproducts and the possible contamination of the desired product with excess epoxide). Although the maximum epoxide concentration is not narrowly limited for the purpose of this invention, a maximum epoxide concentration in practice typically does not exceed about 5 weight percent of the total weight of the reaction mixture. The concentration of epoxide preferably at least about equals, and more preferably somewhat exceeds, a stoichiometric concentration required for the epoxide to interact with each phosphorous acid molecule produced during phosphite degradation. Typically, one epoxide group is required to interact with each phosphorous acid molecule. An excess of epoxide typically is not harmful and a stoichiometric deficiency of epoxide merely limits the effectiveness of its use. Preferably, the epoxide concentration is maintained between about 0.01 and 2 weight percent based on the total weight of reaction mixture. Most preferably, the epoxide concentration is maintained between about 0.1 and 1 weight percent based on total weight of reaction mixture.

The epoxide may be added to and thoroughly mixed into the reaction mixture using any convenient procedure. The epoxide can be mixed with or dissolved in any of the reactant streams or solvent make-up streams or the epoxide periodically can be separately added to the reactant mixture. The epoxide can be added reaction mixture in small quantity over an extended period of operation. In this way, a concentration of epoxide effective to stabilize ligand during steady-state operation is obtained, with epoxide consumed by reaction with phosphorous acid as it is formed. The epoxide also can be added intermittently at a higher concentration, with the intent of achieving a long-term stabilization effect by starting at a higher-than-necessary concentration and allowing the concentration to fall to a more typical concentration during a period without injection addition.

Without wishing to be bound by any particular theory, it appears that the following sequence of reactions may occur:

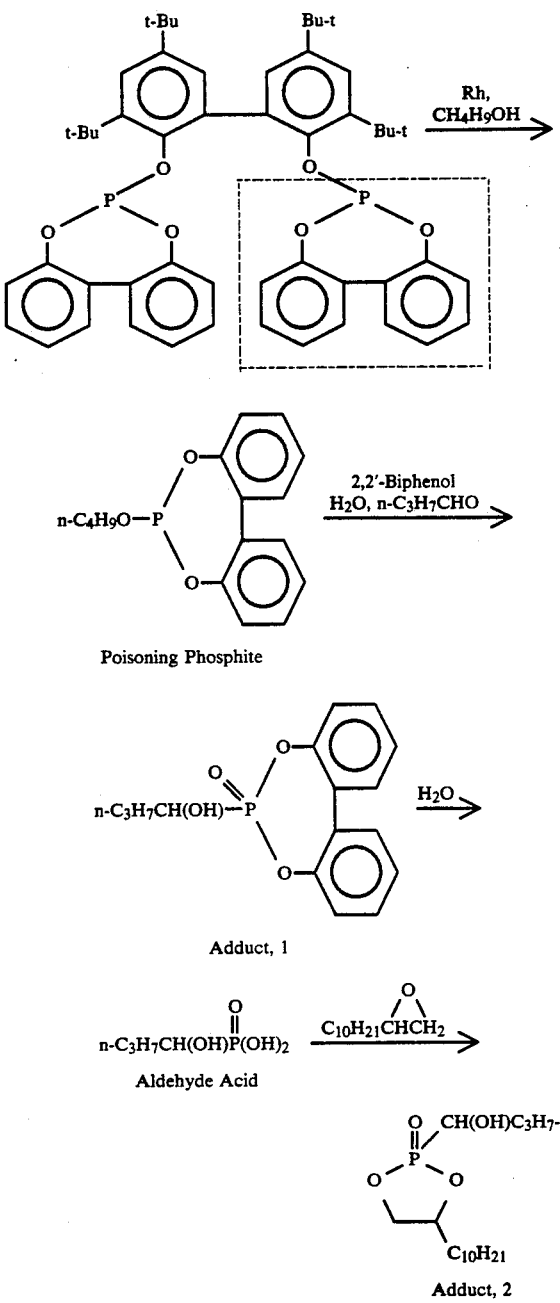

Accordingly the end result is the formation of relatively inert adducts (e.g., Adduct 2 in the above reaction sequence).

Thus as pointed out herein, a noticeable decrease in the catalytic activity of heretofore conventional continuous rhodium-bisphosphite complex catalyzed continuous hydroformylation processes has been observed to occur over time. This intrinsic loss in catalytic activity manifests itself in terms of a measurable drop in productivity and is considered to be caused by in situ formation of a monophosphite ligand by-product that poisons the rhodium- bisphosphite complex catalyst, as described herein. Accordingly a basic point of novelty of this invention rests in the discovery that such intrinsic catalyst deactivation in such hydroformylation processes may be reversed or significantly minimized by carrying out the hydroformylation process in the presence of added water, or a weakly acidic compound, or both added water and weakly acidic compound. For example, rhodium-bisphosphite ligand complex catalysts which have become partially deactivated due to the in situ build-up of undesirable monophosphite ligand by-product may have at least some of their catalytic activity restored by the practice of this invention. Alternatively, it is preferred not to allow for any significant intrinsic catalyst deactivation due to in situ build-up of such monophosphite ligand by-product in the hydroformylation reaction medium, but rather to prevent or at least greatly minimize such deactivation from taking place in the first place by carrying out the hydroformylation process right from its start in the presence of the added water and/or weakly acidic compound additive, so as to hydrolyze any such undesirably monophosphite ligand as quickly as it is produced in situ.

The improvement in the hydroformylation catalytic activity of a rhodium-bisphosphite complex catalyst obtained according to this invention may be determined and confirmed by any suitable conventional procedure for ascertaining an increase in the productivity of the process. Preferably the process of this invention may be easily evaluated by carrying out comparative hydroformylation reactions and continuously monitoring their rates of hydroformylation. The difference in hydroformylation rate (or difference in catalyst activity) may then be observed in any convenient laboratory time frame. For instance, reaction rate may be expressed in terms of gram-moles of aldehyde product produced per liter of catalyst solution per hour of reaction, which rate, if desired, may be adjusted for varying olefin partial pressures by dividing said rate by the olefin partial pressure. Alternatively, if desired, the presence of such undesirable monophosphite ligands in the hydroformylation reaction medium may be readily monitored and characterized by conventional analytical techniques, such as e.g. Phosphorus-31 nuclear magnetic resonance spectroscopy and Fast Atom Bombardment Mass Spectroscopy. Thus the process of this invention provides an excellent means for improving the hydroformylation catalytic activity of a solubilized rhodium-bisphosphite complex hydroformylation catalyst as described herein.

Of course it is to be understood that while the optimization of the subject invention necessary to achieve the best results and efficiency desired are dependent upon one's experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or by simple routine experimentation.

Finally, the aldehyde products of the hydroformylation process of this invention have a wide range of utility that is well known and documented in the prior art e.g. they are especially useful as starting materials for the production of alcohols and acids.

The following examples are illustrative of the present invention and are not be regarded as limitative. It is to be understood that all of the parts, percentages and proportions referred to herein and in the appended claims are by weight unless otherwise indicated.

EXAMPLE 1

Propylene was continuously hydroformylated to produce butyraldehyde in the following manner.

The hydroformylation was conducted in a glass reactor operating in a continuous single pass propylene hydroformylation mode. The reactor consisted of a three-ounce pressure bottle submersed in an oil bath with a glass front for viewing. About 20-mL of a freshly prepared rhodium catalytic precursor solution was charged to the reactor with a syringe, after purging the system with nitrogen. The precursor solution contained about 200 ppm rhodium introduced as rhodium dicarbonyl acetylacetonate, about 2.0 weight percent of 6,6'[[3,3',5,5'-tetrakis (1,1-dimethylethyl) 1,1'-biphenyl-2,2'-diyl]bis(oxy)] bis-dibenzo[d,f][1,3,2]-dioxaphosphepin ligand (about 12 mole equivalents per mole equivalent of rhodium), about 2.0 weight percent biphenol (i.e. 2,2'-dihydroxybiphenyl) as the weakly acidic additive, and Texanol® (2,2,4-trimethyl -1,3-pentanediol monoisobutyrate) as the solvent. After closing the reactor, the system was again purged with nitrogen and the oil bath was heated to furnish the desired hydroformylation reaction temperature. The hydroformylation reaction was conducted at a total gas pressure of about 160 psig., the partial pressures of hydrogen, carbon monoxide, and propylene being given in Table 1 below, the remainder being nitrogen and aldehyde product. The flows of the feed gases (carbon monoxide, hydrogen, proplene and nitrogen) were controlled individually with mass flow meters and the feed gases dispersed into the precursor solution via fritted spargers. The reaction temperatures are given in Table 1 below. The unreacted portion of the feed gases was stripped out the butyraldehyde product and the outlet gas analyzed over about 6 days of continuous operation. The approximate daily average reaction rate in terms of gram-moles per liter per hour of product butyraldehydes divided by propylene partial pressure, as well as the linear (n-butyraldehyde) to branched (2-methylpropionaldehyde) product ratio are given in Table 1 below.

TABLE 1

| Days Opern. | Temp. °C. | Rhodium ppm* | Partial Pressures | | | Reaction Rate g-mole/L/Hr | Linear/ Branched C₄ |
| | | | CO psia | H₂ psia | Propylene psia | Propylene Partial Pressure | Aldehyde Mole Ratio |
| --- | --- | --- | --- | --- | --- | --- | --- |
| 1 | 100 | 190 | 45 | 43 | 2.0 | 2.0 | 29 |
| 2 | 100 | 193 | 43 | 44 | 2.8 | 1.3 | 31 |
| 3 | 100 | 200 | 47 | 46 | 4.2 | 0.80 | 32 |
| 4 | 100 | 208 | 49 | 45 | 6.0 | 0.54 | 32 |
| 5 | 100 | 216 | 43 | 45 | 7.4 | 0.37 | 32 |
| 6 | 100 | 211 | 46 | 45 | 7.3 | 0.35 | 33 |

*Changing values reflect change in daily ligand reactor solution levels.

After an initial reaction rate of about 2.0 for day one, the catalyst activity slowly declined until it became relatively constant (this activity being referred to herein as the lined-out activity), e.g., note the average reaction rate of about 0.36 over days 5 and 6 of the experiment.

In contrast, a comparative test carried out in essentially the same matter and using the same ingredients and amounts as noted above, save for omitting the weakly acidic additive i.e. biphenol, was also found to provide a reaction rate of about 2.0 for day 1. However this comparative process carried out in the absence of said biphenol exhibited an average reaction rate of about 0.20 over days 5 and 6 of the comparative experiment.

Said comparison indicates that when compared to the catalyst profile of a catalyst solution containing no biphenol, the lined-out reaction rate activity of the catalyst solution containing said biphenol was much higher.

EXAMPLES 2 TO 24

A series of rhodium complex catalyst precursor solutions were employed to hydroformylate propylene. The same procedure, ingredients and reaction conditions of Example 1 were employed with the exception that various different weakly acidic additive compounds were employed in place of the biphenol of Example 1. The approximate lined-out average reaction rate in terms of gram-moles of butyraldehyde per liter of catalyst solution per hour divided by propylene partial pressure for each experiment is given in Table 2 below along with the particular weakly acidic additive employed. Also reported is the percent catalyst activity improvement of each experiment over a comparative catalyst solution that did not contain any weakly acidic additive, said catalyst solution having been assigned a comparative activity rating of 100 percent.

cent of said Ligand A. A precursor solution containing 200 ppm of rhodium in the form of Rh (Ligand A) CO(BPBP)(H), 2.0 weight percent of Ligand A and 5 mole equivalents of BPBP ligand (i.e. the catalyst inhibitor or poisoning phosphite) was charged to the second reactor (Reactor 2). Another precursor solution containing 200 ppm rhodium in the form of Rh(Ligand A) CO(BPBP)H, 2.0 weight percent Ligand A and 5 mole equivalents of BPBP ligand together with 2.0 weight percent of biphenol (i.e., 2,2'-dihydroxybiphenyl) as the weakly acidic additive was charged to the third reactor (Reactor 3). Ligand A represents a 6,6'[[3,3',5,5'-tetrakis(1,1-dimethylethyl) 1,1'-biphenyl-2,2'-diyl]bis-(oxy)] bis-dibenzo[d,f] [1,3,2]-dioxaphosphepin ligand, while BPBP represents a n-butyl[1,1'-biphenol-2,2'-diyl] phosphite ligand. The same hydroformylation procedure and reaction conditions of Example 1 were employed in all three reactors and the reactivity of all three catalyst systems were monitored. After 50 hours, the catalyst systems of Reactors 2 and 3 were observed to have practically zero activity. At this point about 0.50 mL of water was added to each of Reactors 2 and 3 and the activities of the catalyst systems of these two reactors were observed to increase. The lined-out approximate average reaction rate of each catalyst solution in terms of gram moles per liter per hour of butyraldehyde product divided by propylene partial pressure observed for each experiment is given in Table 3 below.

TABLE 3

| Reactor # | Content | Treatment | Reaction Rate before treatment | Reaction Rate after treatment |
|---|---|---|---|---|
| 1 | Rh Ligand A | None | 0.32 | 0.32 |
| 2 | Rh Ligand A BPBP | $H_2O$ | zero | 0.28 |
| 3 | Rh Ligand A BPBP biphenol | $H_2O$ | zero | 0.60 |

TABLE 2

| Example # | Additive | $pK_a$ | Wt. % | % Catalyst Activities | Reaction Rate g-mole/L/Hr Propylene Partial Pressure |
|---|---|---|---|---|---|
| Comparison | none | | | 100 | 0.20 |
| 2 | 2,2'-dinapthol | 9.2 (est.) | 2.0 | 120 | 0.24 |
| 3 | 4,4'-Dimethoxy-2,2'-biphenol | 7.5 (est.) | 2.0 | 160 | 0.32 |
| 4 | 4,4-Di-tert-butyl-2,2'-biphenol | 9.5 (est.) | 2.0 | 150 | 0.30 |
| 5 | 4,4-Dibromo-2,2'-biphenol | 7.5 (est.) | 2.0 | 180 | 0.36 |
| 6 | Catechol | 9.36 | 2.0 | 170 | 0.34 |
| 7 | m-trifluoromethylphenol | 8.95 | 3.5 | 160 | 0.32 |
| 8 | 3,5-bis(trifluoromethyl)phenol | 8.0 (est.) | 2.0 | 160 | 0.32 |
| 9 | 4-chlorophenol | 9.43 | 2.0 | 150 | 0.30 |
| 10 | 2,4-dichlorophenol | 7.85 | 4.0 | 200 | 0.40 |
| 11 | 3,5-dichlorophenol | 8.18 | 4.0 | 200 | 0.40 |
| 12 | 4-nitrophenol | 7.15 | 2.0 | 200 | 0.40 |
| 13 | benzoic acid | 4.20 | 2.0 | 200 | 0.40 |
| 14 | Salicylic acid | 2.98 | 2.0 | 160 | 0.32 |
| 15 | 4-Ethoxybenzoic acid | 4.8 | 2.0 | 300 | 0.60 |
| 16 | 4-trifluoromethylbenzoic acid | 4.0 (est.) | 2.0 | 200 | 0.40 |
| 17 | 4-nitrobenzoic acid | 3.44 | 2.0 | 220 | 0.44 |
| 18 | 4-tert-butylbenzoic acid | 4.39 | 2.0 | 145 | 0.29 |
| 19 | picolinic acid | 5.29 | 1.5 | 150 | 0.30 |
| 20 | 3,5-dihydroxybenzoic acid | 4.04 | 2.0 | 155 | 0.31 |
| 21 | 3,5-Dimethoxybenzoic acid | 4.0 (est.) | 2.0 | 175 | 0.35 |
| 22 | phthalic acid | 2.95 | 1.0 | 173 | 0.35 |
| 23 | isophthalic acid | 3.54 | 1.0 | 170 | 0.34 |
| 24 | isophthalic acid | 3.54 | 0.5 | 150 | 0.30 |

EXAMPLE 25

The continuous single pass hydroformylation process of Example 1 directed to hydroformylating propylene was repeated using three separate single pass reactors. A precursor solution containing 200 ppm Rh in the form of Rh(Ligand A)(CO)$_2$H was charged into the first reactor (Reactor 1) together with 2.0 weight per-

EXAMPLE 26

A mixed olefin starting material [butene-1 and butene-2 (cis and trans)] was hydroformylated for 124 days as follows: A liquid recycle reactor system was employed which contained two 2.8 liter stainless steel stirred tank reactors (Reactors 1 and 2) connected in series. Each reactor had a vertically mounted agitator and a circular tubular sparger near the bottom for feeding the olefin and/or syn gas to the reactor. The sparger contained a plurality of holes of sufficient size to provide the desired gas flow into the liquid body. Each reactor contained a silicone oil shell as means of bringing the contents of the reactor up to reaction temperature and each reactor contained internal cooling coils for controlling the reaction temperature. Reactors 1 and 2 were connected via a line to transfer any unreacted gases from Reactor 1 to Reactor 2 and were further connected via a line so that a portion of the liquid reaction solution containing aldehyde product and catalyst from Reactor 1 could be pumped into Reactor 2. Hence the unreacted olefin of Reactor 1 was further hydroformylated in Reactor 2.

Each reactor also contained a pneumatic liquid level controller for automatic control of the liquid levels in the reactors. Reactor 1 further contained a line for introducing the olefin, carbon monoxide and hydrogen through the sparger while make up carbon monoxide and hydrogen was added to Reactor 2 via a transfer line that also carried the unreacted gases from Reactor 1 to Reactor 2. Reactor 2 also contained a blow-off vent for removal of the unreacted gases. A line from the bottom of Reactor 2 was connected to the top of a vaporizer so that a portion of the liquid reaction solution could be pumped from Reactor 2 to the vaporizer. Vaporized aldehyde was separated from the non-volatilized components of the liquid reaction solution in the gas-liquid separator part of the vaporizer. The remaining non-volatilized solution was pumped through a recycle line back into Reactor 1. The recycle line also contained a pneumatic liquid level controller. The vaporized aldehyde product was passed into a water cooled condenser, liquified and collected in a product receiver.

The hydroformylation reaction was conducted by charging to Reactor 1 one liter of catalyst precursor solution comprising rhodium dicarbonyl acetylacetonate (about 125 ppm rhodium), about 0.75 wt. % of 6,6'[[3,3',5,5'-tetrakis(1,1-dimethylethyl) 1,1'-biphenyl-2,2'-diyl]bis(oxy)]bis-dibenzo[d,f][1,3, 2]-dioxaphosphepin ligand (about 7.4 mole equivalents of ligand per mole equivalent of rhodium), 3.75 wt. % of biphenol (i.e. 2,2'-dihydroxybiphenyl) as the weakly acidic additive, and, as solvent, about 10 wt. % of tetraethylene glycol dimethyl ether and about 85.5 wt. % of $C_5$ aldehyde (n-valeraldehyde and 2-methylbutyraldehyde in the ratio of about 30:1). Reactor 2 was charged with the same amounts of the same precursor solution. The reactors were then purged with nitrogen to remove any oxygen present. Then about 100 psig of nitrogen pressure was put on both reactors and the reactors were heated to the reaction temperatures shown in the Table 4. Controlled flows of purified hydrogen, carbon monoxide and a mixed butenes [1-butene and butene-2 (cis and trans)] were fed through the sparger into the bottom of Reactor 1 and the reactor pressure was increased to the operating pressure given in the Table 4. When the liquid level in Reactor 1 started to increase as a result of liquid aldehyde product formation, a portion of the liquid reaction solution was pumped from Reactor 1 to Reactor 2 through a line at the top of Reactor 2 at a rate sufficient to maintain a constant liquid level in Reactor 1. The pressure of Reactor 2 increased to its operating pressure given in the Table 4. Blow-off gas from Reactor 2 was collected and measured. A controlled flow of make-up syn gas (CO and $H_2$) was added to Reactor 2 in order to maintain their desired partial pressures in Reactor 2. The above-mentioned operating pressures and reaction temperatures were maintained throughout the hydroformylation. As the liquid level in Reactor 2 started to increase as a result of liquid aldehyde product formation, a portion of the liquid reaction solution was pumped to the vaporizer/separator at a rate sufficient to maintain a constant liquid level in Reactor 2. The crude aldehyde product was separated at 109° C. and 24.7 psia from the liquid reaction solution, condensed and collected in a product receiver. The non-volatized catalyst-containing liquid reaction solution remaining in Reactor 2 was recycled back to Reactor 1.

Every third day over the course of the 124 day run, 2 milliliters of 1,2-epoxydodecane was fed into each of Reactors 1 and 2 via a valve fitted with a septum in the bottom of each reactor to give an epoxide concentration after each addition of about 0.2% in each reactor.

The hydroformylation of the mixed butene feed was continued for 124 days. The hydroformylation reaction conditions as well as the rate of $C_5$ aldehydes produced (in terms of gram moles per liter per hour) and the linear to branched aldehyde product ratio (n-valeraldehyde to 2-methylbutyraldehyde) are shown in the Table 4. The activity of the catalyst was constant over the 124 day course of the run as shown in the Table 4. This constant activity indicates that excessive ligand degradation had not occurred over the course of the run.

TABLE 4

| Days of Operation | 2 | 21 | 41 | 81 | 124 |
|---|---|---|---|---|---|
| Reactor 1 | | | | | |
| °C. | 85 | 85 | 85 | 85 | 85 |
| $H_2$, psia | 79.8 | 88.4 | 83.1 | 98.1 | 99 |
| CO, psia | 90.9 | 91.5 | 88.5 | 81.6 | 89.1 |
| 1-$C_4H_8$, psia | 6.4 | 10.5 | 14.8 | 7.5 | 5.4 |
| 2-$C_4H_8$, psia | 42.3 | 27.6 | 35.2 | 36 | 36.9* |
| Reactor 2 | | | | | |
| °C. | 90 | 95 | 85 | 85 | 85 |
| $H_2$, psia | 68.6 | 78.8 | 74.5 | 74.7 | 96.7 |
| CO, psia | 87.3 | 81.7 | 85.2 | 87.3 | 84.7 |
| 1-$C_4H_8$, psia | 0.8 | 1 | 1.5 | 1.2 | 1.1 |
| 2-$C_4H_8$, psia | 31.9 | 23 | 29.4 | 30.3 | 33.7** |
| Results | | | | | |
| $C_5$ aldehydes, gmols/L/Hr | 1.489 | 1.706 | 1.751 | 1.847 | 1.832 |
| Linear/branched aldehyde ratio | 32.3 | 31.2 | 30.3 | 35.9 | 30.0 |

*There was an average pressure of 16.2 psia due to the cis isomer and an average pressure of 14.3 psia in Reactor 1 due to trans isomer over the 124 days of the run
**There was an average of 16.9 psia due to the cis isomer and an average pressure of 11.9 psia in Reactor 2 due to trans isomer over the 124 days of the run

EXAMPLE 27

Following the procedure set out in Example 26 above, two reactors were employed in series to hydroformylate mixed butenes. The same partial pressures of the reactant gases were employed and the same concentrations of rhodium and ligand were used as in Example 26 above. This run differed from the run of Example 26 in the employment of 3,4-epoxycyclohexylmethyl-3,4-epoxycyclohexane carboxylate in place of the 1,2- epoxydodecane. The rate of formation of $C_5$ aldehyde products on the first day of this run was 2.11 gmols/L/Hr and the rate of formation of aldehyde products on the twenty-second day of this run was 1.71 gmols/L/Hr. There was no evidence of significant ligand degradation over this period of operation.

EXAMPLE 28

In a continuous catalyst liquid recycle manner, propylene was hydroformylated for 17 days in a similar manner as described in Example 26 using a single reactor. A solution comprising rhodium dicarbonyl acetylacetonate (about 200 ppm rhodium), about 2.0 wt. % of 6,6′[[3,3′,5,5′-tetrakis (1,1-dimethylethyl)1,1′-biphenyl-2,2′-diyl]bis(oxy)] bis-dibenzo[d,f][1,3,2]-dioxaphosphepin ligand (about 12 mole equivalents of ligand per mole equivalent of rhodium), 2.0 wt. % of biphenol (i.e., 2,2′-dihydroxybiphenyl) as the weakly acidic additive, and, as solvent, about 10 wt. % of tetraglyme (tetraethylene glycol dimethyl ether) and about 86 wt. % of $C_4$ aldehyde (n-butyraldehyde and iso-butyraldehyde) was employed. No other additive, save for the propylene, carbon monoxide and hydrogen reactants, was added to the reaction medium.

The hydroformylation of the propylene feed was continued for 17 days. The hydroformylation reaction conditions as well as the rate of butyraldehydes produced (in terms of gram moles of aldehyde product per liter of catalyst solution per hour of reaction divided by the propylene partial pressure) and the linear to branched aldyhyde product ratio (n-butyraldehyde to iso-butyraldehyde) are shown in Table 5, below.

A comparative experiment was conducted in a similar manner as described above, except that no biphenol was employed. Again the hydroformylation was continued for 17 days. The hydroformylation reaction conditions of this comparison as well as the rate of butyraldehydes produced and the linear to branched aldehyde product ratio (n-butyraldehyde to iso-butyraldehyde) are also shown in Table 5, below.

TABLE 5

| Days Operation | With Biphenol* Reaction Rate g-mole/L/Hr Propylene Partial Pressure | Without Biphenol** Reaction Rate g-mole/L/Hr Propylene Partial Pressure |
|---|---|---|
| 3 | 0.8 | 0.65 |
| 8 | 0.77 | 0.52 |
| 9 | 0.75 | 0.50 |
| 12 | 0.73 | 0.37 |
| 15 | 0.77 | 0.35 |
| 17 | 0.75 | 0.41 |

*Average Operating Reactor Conditions:

TABLE 5-continued

| Days Operation | With Biphenol* Reaction Rate g-mole/L/Hr Propylene Partial Pressure | Without Biphenol** Reaction Rate g-mole/L/Hr Propylene Partial Pressure |
|---|---|---|
| Reaction Temperature | 85° C. | |
| Rhodium Conc. | 84 ppm | |
| Propylene Partial Pressure | 31 psi | |
| CO Partial Pressure | 67 psi | |
| $H_2$ Partial Pressure | 68 psi | |

**Average Operating Reactor Conditions
| Reaction Temperature | 85° C. |
| Rhodium Conc. | 95 ppm |
| Propylene Partial Pressure | 45 psi |
| CO Partial Pressure | 58 psi |
| $H_2$ Partial Pressure | 59 psi |

The above results clearly demonstrate the effectiveness of the addition of the acidic additive, biphenol, in enhancing the catalyst activity of the process.

EXAMPLE 29

Propylene was continuously hydroformylated to produce butyraldehyde in a similar manner as described in Example 1.

The catalyst precursor solution contained about 200 ppm rhodium introduced as rhodium dicarbonyl acetylacetonate, about 2.0 weight percent of 6,6′[[3,3′,5,5′-tetrakis(1,1-dimethylethyl)1,1′-biphenyl-2,2′-diyl]bis(oxy)]bis-dibenzo [d,f][1,3,2]-dioxaphosphepin ligand (about 12 mole equivalents per mole equivalent of rhodium), and about 98 weight percent of a 50:50 mixture of tetraglyme (tetraethylene glycol dimethyl ether) and 2-pyrolidone as the solvent. The effect of adding water to the catalyst containing reaction medium was determined by employing syn gas ($CO+H_2$) that was deliberately saturated with water in this experiment via purging the syn gas through a water tower prior to charging it to the reaction medium. The hydroformylation reaction was monitored as described in Example 1 over eight days of continuous operation. The approximate daily average reaction rate in terms of gram moles of aldehyde product per liter of catalyst solution per hour of reaction divided by propylene partial pressure, as well as the linear (n-butyraldehyde) to branched (iso-butyraldehyde) product ratio are given in Table 6 below.

TABLE 6

| Days Opern. | Temp. °C. | Rhodium ppm | Partial Pressures | | | Reaction Rate g-mole/L/Hr Propylene Partial Pressure | Linear/ Branched $C_4$ Aldehyde Mole Ratio |
| | | | CO psia | $H_2$ psia | Propylene psia | | |
|---|---|---|---|---|---|---|---|
| 1.1 | 100 | 124 | 45 | 45 | 2.7 | 0.73 | 32 |
| 2.3 | 100 | 136 | 49 | 49 | 2.1 | 0.67 | 46 |
| 3.0 | 100 | 145 | 47 | 48 | 2.7 | 0.65 | 42 |
| 4.0 | 100 | 145 | 47 | 48 | 3.0 | 0.62 | 43 |
| 5.2 | 100 | 145 | 47 | 48 | 2.8 | 0.62 | 43 |
| 6.0 | 100 | 145 | 45 | 46 | 3.3 | 0.63 | 33 |
| 7.2 | 100 | 144 | 45 | 46 | 3.1 | 0.67 | 38 |
| 8.1 | 100 | 145 | 45 | 45 | 3.1 | 0.66 | 36 |

A comparative experiment was conducted in a similar manner as described above, except that the syn gas ($CO+H_2$) used was not saturated with water and no water or weakly acidic additive was added to the catalyst system. The hydroformylation was monitored in the same manner over eight days of continuous operation and the data collected is given in Table 7 below.

TABLE 7

| Days Opern. | Temp. °C. | Rhodium ppm | Partial Pressures | | | Reaction Rate g-mole/L/Hr Propylene Partial Pressure | Linear/ Branched C4 Aldehyde Mole Ratio |
| --- | --- | --- | --- | --- | --- | --- | --- |
| | | | CO psia | H2 psia | Propylene psia | | |
| 1.2 | 100 | 121 | 45 | 45 | 2.6 | 0.63 | 31 |
| 2.2 | 100 | 124 | 45 | 45 | 3.6 | 0.52 | 31 |
| 3.1 | 100 | 126 | 45 | 46 | 4.2 | 0.43 | 32 |
| 4.0 | 100 | 130 | 46 | 46 | 5.3 | 0.33 | 35 |
| 5.1 | 100 | 135 | 46 | 46 | 6.1 | 0.28 | 42 |
| 6.1 | 100 | 138 | 46 | 47 | 6.4 | 0.28 | 33 |
| 7.2 | 100 | 142 | 46 | 46 | 6.9 | 0.26 | 42 |
| 8.1 | 100 | 143 | 46 | 45 | 7.1 | 0.26 | 37 |

A comparison of the data in Tables 6 and 7 clearly shows the beneficial effects obtained in terms of improved catalyst performance when employing water saturated syn gas as opposed to carrying out the same process in the absence of any added water.

EXAMPLE 30

In a continuous catalyst liquid recycle manner, propylene was hydroformylated for 52 days in a similar manner as described in Example 26, using a single reactor. A liter of catalyst solution comprising rhodium dicarbonyl acetylacetonate (about 102 ppm rhodium), about 0.6 wt. % of 6,6′[[3,3′,5,5′-tetrakis(1,1-dimethylethyl) 1,1′-biphenyl-2,2′diyl]bis(oxy)]bis-dibenzo[d,f][1,3, 2]-dioxaphosphepin ligand (about 7.2 mole equivalents of ligand per mole equivalent of rhodium), and, as solvent, about 12 wt. % of tetraethylene glycol dimethyl ether (tetraglyme) and about 85.4 wt. % of C4 aldehyde (n-butyraldehyde and iso-butyraldehyde in the ratio of about 25-30:1) was employed. Water was also added to the reaction system at a rate of about 1000 ppm by weight on a syn gas (CO+H2) basis in the form of water saturated syn gas by sparging a third of the syn gas employed through a tank of water before adding it to the reactor. The water concentration in the reaction solution of the reactor averaged around 0.2 wt. %, although the standard deviation was higher than normal. Subsequent similar experiments have been carried out wherein the water concentration was about 0.2 weight percent. An amount equal to 0.07 volume percent of 1,2-epoxydodecane was added three times per week to scavenge acids that may form in the reaction system. No other additive was added to the reaction medium.

The hydroformylation of the propylene feed was continued for 52 days. The hydroformylation reaction conditions as well as the rate of butyraldehydes produced (in terms of gram moles of aldehyde product per liter of catalyst solution per hour of reaction) and the linear to branched aldyhyde product ratio (n-butyraldehyde to iso-butyraldehyde) are shown in Table 8, below.

TABLE 8

| Average Operating Conditions and Catalyst Performance | | |
| --- | --- | --- |
| | Average | Range |
| Days Operation | 52.5 | — |
| Operating Reactor Conditions | | |
| Pres., psia | 175.7 | 184.7–106.7 |
| Temp., °C. | 85.0 | — |
| Rhodium Conc. ppmw | 61 | 47–71 |
| Ligand Conc., wt % | 0.39 | 0.51–0.29 |
| Aldehyde Conc., wt % | 85.2 | 90–80 |
| CO Partial Pressure, psi | 53.4 | 60–30 |
| H2 Partial Pressure, psi | 53.3 | 63–30 |
| C3H6 Partial Pressure, psi | 40 | 53–22 |

TABLE 8-continued

| Average Operating Conditions and Catalyst Performance | | |
| --- | --- | --- |
| | Average | Range |
| Operating Vaporizer Conditions | | |
| Temp., °C. | 104.5 | 100–125 |
| Pres., psi | 23.5 | 25.7–22.2 |
| Feed/Tails Ratio | 3.75 | 8.9–2.2 |
| Average Catalyst Performance | | |
| Aldehyde Rate, gmole/L/hr | 3.6 | 4.1–3.1 |
| Isomer Ratio (n:iso) | 22.7 | 32–2.7 |
| Propane Selectivity, % | 2.3 | 2.7–1.3 |
| Heavies Selectivity, % | 0.05 | |
| Heavies Rate, g/L/hr | 0.2 | |

In the above experiment, after eight days of operation all the free ligand had been oxidized due to an inadvertent unknown source of oxygen. Loss of all the free ligand produced a sharp drop in aldehyde product isomer ratio and an increase in the observed activity of the catalyst. Fresh make-up ligand was added and the reaction unit began operating normally again without evidencing any rhodium loss. Syn gas partial pressures were periodically lowered briefly from 60 psi each to 30 psi each to check the kinetic responses of the gases. Ligand consumption during the run excluding the initial oxidation problem was 0.14 g/L/day. Phosphorus NMR of the catalyst solution showed no unusual behavior regarding ligand decomposition. Poisoning phosphite was not evident in the spectra following the first oxidation of the ligand. The vaporizer temperature was held at about 100° C. for most of the run and catalyst activity was steady. When the vaporizer temperature was increased to 115° C. a decline in catalyst activity was observed which increased sharply when the vaporizer temperature was increased to 125° C.

The above experiment clearly demonstrates the effectiveness of the addition of water as a catalytic activity enhancing additive for the hydroformylation process.

Various modifications and variations of this invention will be obvious to a worker skilled in the art and it is to be understood that such modifications and variations are to be included within the purview of this application and the spirit and scope of the appended claims.

What is claimed is:

1. An improved continuous hydroformylation process for producing aldehydes which comprises reacting an olefinically unsaturated compound containing from 2 to 30 carbon atoms with carbon monoxide and hydrogen in the presence of a solubilized rhodium-bisphosphite complex catalyst wherein the bisphosphite ligand of said complex catalyst is a ligand selected from the class consisting of

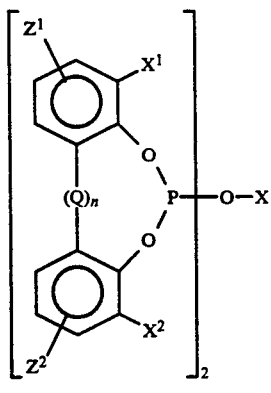

(I)

and

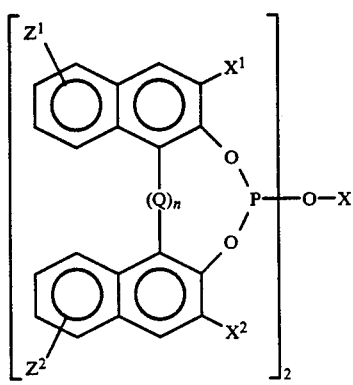

(II)

wherein each $X^1$ and $X^2$ radical individually represents a radical selected from the group consisting of hydrogen, methyl, ethyl and n-propyl; wherein each $Z^1$ and $Z^2$ radical individually represents hydrogen or a substituent radical containing from 1 to 18 carbon atoms; wherein each X represents a divalent radical selected from the group consisting of alkylene, alkylene-oxo-alkylene, arylene and arylene-$(Q)_n$-arylene, and wherein each alkylene radical individually contains from 2 to 18 carbon atoms and is the same or different, and wherein each arylene radical individually contains from 6 to 18 carbon atoms and is the same or different; wherein each Q individually represents a —$CR^5R^6$—divalent bridging group and each $R^5$ and $R^6$ radical individually represents hydrogen or a methyl radical; and wherein each n individually has a value of 0 or 1; the improvement comprising carrying out said process in the presence of minor amount of a catalytic activity enhancing additive present in the hydroformylation reaction medium of the process, said additive being selected from the class consisting of added water, a weakly acidic compound having a pKa value of from about 1.0 to about 12, or both added water and a weakly acidic compound having a pKa value of from about 1.0 to about 12, and wherein said weakly acidic compounds are aryl compounds containing form 1 to 3 substituent radicals directly bonded thereto, each said substituent being individually selected from the group consisting of hydroxy and carboxylic acid radicals.

2. A process as defined in claim 1 wherein said minor amount of catalytic activity enhancing additive employed ranges from about 0.05 to about 20 weight percent based on the total weight of the hydroformylation reaction medium.

3. A hydroformylation process as defined in claim 2, wherein the amount of added water employed ranges from 0 to about 20 weight percent based on the total weight of the hydroformylation reaction medium.

4. A hydroformylation process as defined in claim 2, wherein the amount of weakly acidic compound employed ranges from 0 to about 20 weight percent based on the total weight of the hydroformylation reaction medium.

5. A hydroformylation process as defined in claim 3, wherein the amount of added water employed ranges from about 0.05 to about 10 weight percent based on the total weight of the hydroformylation medium.

6. A hydroformylation process as defined in claim 4, wherein the amount of weakly acidic compound employed ranges from about 1 to about 5 weight percent based on the total weight of the hydroformylation reaction medium.

7. A process as defined in claim 4, wherein the weakly acidic compound is 2,2'-dihydroxybiphenyl.

8. A process as defined in claim 6, wherein the weakly acidic compound is 2,2'-dihydroxybiphenyl.

9. A process as defined in claim 5, wherein the process is carried out in the absence of any said weakly acidic compound additive.

10. A process as defined in claim 2, wherein the bisphosphite ligand employed is a ligand selected from the class consisting of

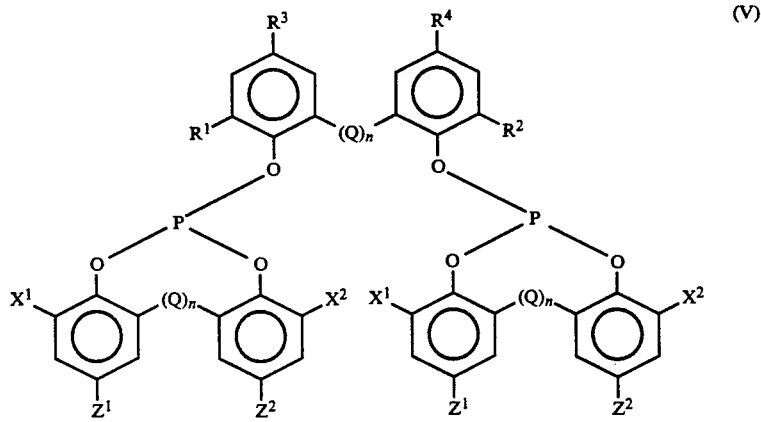

(V)

and (VI)

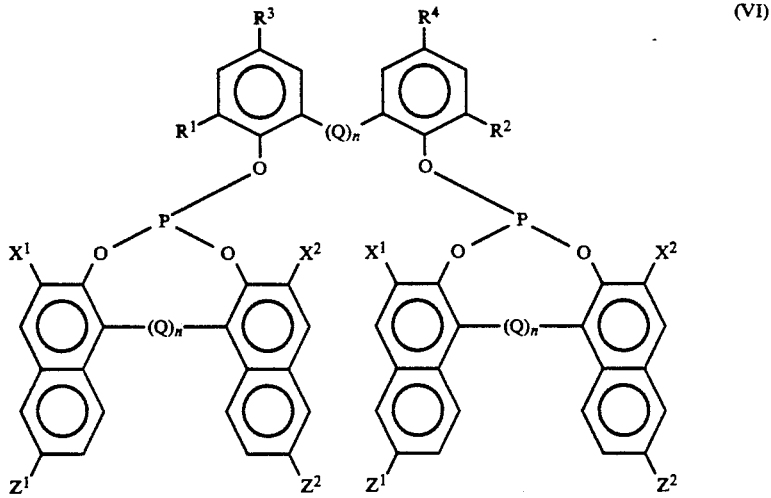

wherein each $Z^1$, $Z^2$, $R^3$ and $R^4$ radical individually represents a radical selected from the group consisting of hydrogen, an alkyl radical having from 1 to 8 carbon atoms, phenyl, benzyl, cyclohexyl and 1-methylcyclohexyl, hydroxy and an alkoxy radical having from 1 to 8 carbon atoms; wherein each $R^1$ and $R^2$ individually represents a radical selected from the group consisting of a branched alkyl radical having from 3 to 8 carbon atoms, cyclohexy and 1-methylclohexyl; and wherein $X^1$, $X^2$, Q and n are the same as defined above.

11. A process as defined in claim 2, wherein an epoxide compound is also present in the hydroformylation reaction medium.

12. A process as defined in claim 5, wherein the bisphosphite ligand is 6,6'[[3,3', 5,5'-tetrakis (1,1-dimethylethyl) 1,1'-biphenyl-2,2'-diyl] bis (oxy)] bis-dibenzo [d,f] [1,3,2]- dioxaphosphepin.

13. A process as defined in claim 5, wherein the bisphosphite ligand is 6,6'[[3,3', 5,5'-tetrakis (1,1-dimethylpropyl) 1,1'-biphenyl-2,2'-diyl] bis (oxy)] bis-dibenzo [d,f] [1,3,2]-dioxaphosphepin.

14. A process as defined in claim 5, wherein the bisphosphite ligand is 6,6'-[[3,3'-bis (1,1- dimethylethyl)- 5,5'-dimethoxy [1,1'-biphenyl]-2,2'- diyl] bis (oxy)] bis-dibenzo [d,f] [1,3,2]-dioxaphosphepin.

15. A process as defined in claim 10, wherein an epoxide compound is also present in the hydroformylation reaction medium.

16. A process as defined in claim 9, wherein the bisphosphite ligand is 6,6'[[3,3', 5,5'-tetrakis (1,1-dimethylethyl) 1,1'-biphenyl-2,2'-diyl] bis (oxy)] bis-dibenzo [d,f] [1,3,2]- dioxaphosphepin.

17. A process as defined in claim 9, wherein the bisphosphite ligand is 6,6'[[3,3', 5,5'-tetrakis (1,1-dimethylpropyl) 1,1'-biphenyl-2,2'-diyl] bis (oxy)] bis-dibenzo [d,f] [1,3,2]-dioxaphosphepin.

18. A process as defined in claim 9, wherein the bisphosphite ligand is 6,6'-[[3,3'-bis (1,1- dimethylethyl)- 5,5'-dimethoxy [1,1'-biphenyl]-2,2'- diyl] bis (oxy)] bis-dibenzo [d,f] [1,3,2] dioxaphosphepin.

19. A process as defined in claim 9, wherein an epoxide compound is also present in the hydroformylation reaction medium.

20. A process as defined in claim 9, wherein the bisphosphite ligand employed is a ligand selected from the class consisting of (V)

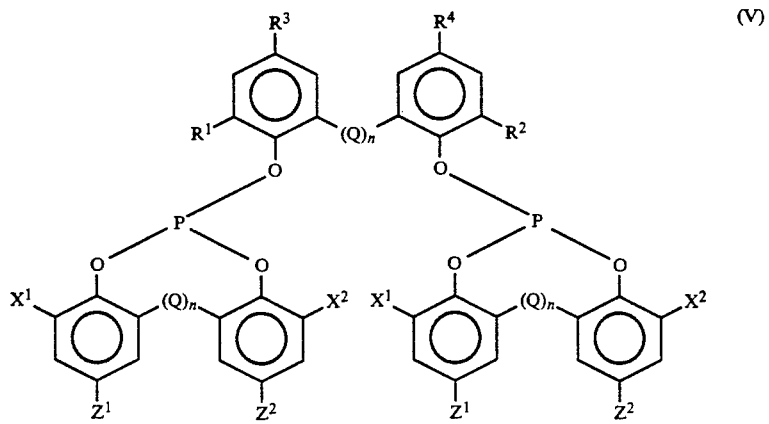

and

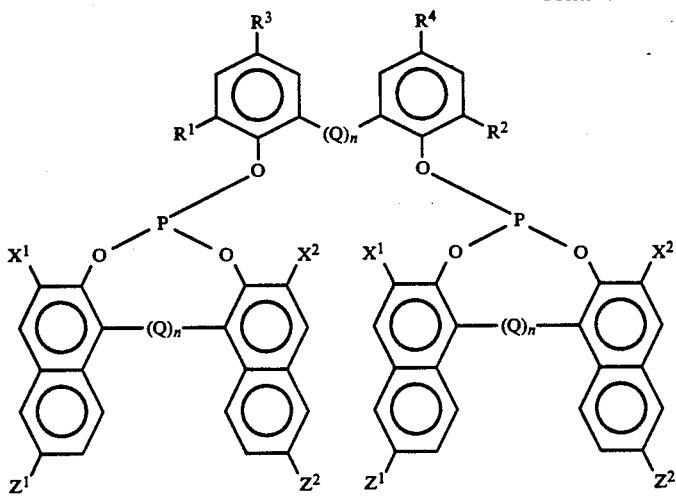

(VI)

wherein each $Z^1$, $Z^2$, $R^3$ and $R^4$ radical individually represents a radical selected from the group consisting of hydrogen, an alkyl radical having from 1 to 8 carbon atoms, phenyl, benzyl, cyclohexyl and 1-methylcyclohexyl, hydroxy and an alkoxy radical having from 1 to 8 carbon atoms; wherein each $R^1$ and $R^2$ individually represents a radical selected from the group consisting of a branched alkyl radical having from 3 to 8 carbon atoms, cyclohexyl and 1-methylcyclohexyl; and wherein $X^1$, $X^2$, Q and n are the same as defined above.

* * * * *